(12) United States Patent
Boudreaux

(10) Patent No.: US 11,033,293 B2
(45) Date of Patent: Jun. 15, 2021

(54) ULTRASONIC TRANSDUCER TO BLADE ACOUSTIC COUPLING, CONNECTIONS, AND CONFIGURATIONS

(71) Applicant: Ethicon LLC, Guaynabo, PR (US)

(72) Inventor: Chad P. Boudreaux, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 240 days.

(21) Appl. No.: 15/994,755

(22) Filed: May 31, 2018

(65) Prior Publication Data

US 2019/0021756 A1    Jan. 24, 2019

Related U.S. Application Data

(63) Continuation-in-part of application No. 15/654,428, filed on Jul. 19, 2017, now abandoned.

(51) Int. Cl.
*A61B 17/32* (2006.01)
*A61B 34/30* (2016.01)
(Continued)

(52) U.S. Cl.
CPC .......... *A61B 17/320092* (2013.01); *A61B 17/00234* (2013.01); *A61B 34/30* (2016.02); *A61B 18/1445* (2013.01); *A61B 34/70* (2016.02); *A61B 2017/003* (2013.01); *A61B 2017/00309* (2013.01); *A61B 2017/00323* (2013.01);
(Continued)

(58) Field of Classification Search
CPC ...... A61B 17/00234; A61B 17/320092; A61B 18/1445; A61B 2017/003; A61B 2017/00309; A61B 2017/00323; A61B 2017/00477; A61B 2017/22018; A61B 2017/2929; A61B 2017/320093;
(Continued)

(56) References Cited

U.S. PATENT DOCUMENTS 5,792,135 A    8/1998   Madhani et al.
5,893,835 A    4/1999   Witt et al.
(Continued)

FOREIGN PATENT DOCUMENTS

EP   1698289 A2   9/2006
EP   3082626 A1   10/2016
(Continued)

OTHER PUBLICATIONS

U.S. Appl. No. 16/012,287, filed Jun. 19, 2018, Surgical Devices and Systems With Rotating End Effector Assemblies Having an Ultrasonic Blade.
(Continued)

*Primary Examiner* — Ashley L Fishback
(74) *Attorney, Agent, or Firm* — Mintz Levin Cohn Ferris Glovsky and Popeo, P.C.

(57) ABSTRACT

Disclosed is a surgical instrument that includes a rotatable shaft having an articulation section and an ultrasonic waveguide disposed within the shaft. The ultrasonic waveguide is configured to articulate at the articulation section. The ultrasonic waveguide is disposed within the shaft. A rotatable clamp arm is located distal of the articulation section of the rotatable shaft. The rotatable clamp arm is configured to rotate independently of the rotatable shaft distal of the articulation section.

9 Claims, 23 Drawing Sheets

(51) Int. Cl.
  *A61B 17/00*  (2006.01)
  *A61B 34/00*  (2016.01)
  *A61B 18/14*  (2006.01)
  *A61B 17/29*  (2006.01)
  *A61B 17/22*  (2006.01)

(52) U.S. Cl.
  CPC .............. *A61B 2017/00477* (2013.01); *A61B 2017/22018* (2013.01); *A61B 2017/2929* (2013.01); *A61B 2017/320093* (2017.08); *A61B 2017/320094* (2017.08); *A61B 2034/305* (2016.02)

(58) Field of Classification Search
  CPC .. A61B 2017/320094; A61B 2034/305; A61B 34/30; A61B 34/70
  See application file for complete search history.

(56) References Cited

U.S. PATENT DOCUMENTS

| | | | |
|---|---|---|---|
| 5,944,737 A | 8/1999 | Tsonton et al. | |
| 6,056,735 A | 5/2000 | Okada et al. | |
| 6,132,368 A | 10/2000 | Cooper | |
| 6,231,565 B1 | 5/2001 | Tovey et al. | |
| 6,364,888 B1 | 4/2002 | Niemeyer et al. | |
| 6,669,690 B1 | 12/2003 | Okada et al. | |
| 6,783,524 B2 | 8/2004 | Anderson et al. | |
| 7,520,865 B2 | 4/2009 | Radley Young et al. | |
| 7,524,320 B2 | 4/2009 | Tierney et al. | |
| 7,621,930 B2 | 11/2009 | Houser | |
| 7,691,098 B2 | 4/2010 | Wallace et al. | |
| 7,780,659 B2 | 8/2010 | Okada et al. | |
| 7,806,891 B2 | 10/2010 | Nowlin et al. | |
| 7,824,401 B2 | 11/2010 | Manzo et al. | |
| 8,574,228 B2 | 11/2013 | Okada et al. | |
| 8,672,935 B2 | 3/2014 | Okada et al. | |
| 8,986,302 B2 | 3/2015 | Aldridge et al. | |
| 9,095,367 B2 | 8/2015 | Olson et al. | |
| 9,351,753 B2 | 5/2016 | Balanev et al. | |
| 9,351,754 B2 | 5/2016 | Vakharia et al. | |
| 9,408,622 B2 | 8/2016 | Stulen et al. | |
| 9,445,816 B2 | 9/2016 | Swayze et al. | |
| 9,585,658 B2 | 3/2017 | Shelton, IV | |
| 10,016,246 B2 | 7/2018 | Yates et al. | |
| 10,149,726 B2 | 12/2018 | Hibner | |
| 2006/0058825 A1 | 3/2006 | Ogura et al. | |
| 2012/0101495 A1* | 4/2012 | Young | A61B 17/29 606/41 |
| 2012/0292367 A1 | 11/2012 | Morgan et al. | |
| 2015/0012021 A1 | 1/2015 | Mihara | |
| 2015/0080924 A1* | 3/2015 | Stulen | A61B 17/320092 606/169 |
| 2015/0164531 A1* | 6/2015 | Faller | A61B 17/320092 606/169 |
| 2015/0209059 A1 | 7/2015 | Trees et al. | |
| 2015/0320437 A1 | 11/2015 | Worrell et al. | |
| 2016/0296250 A1 | 10/2016 | Olson et al. | |
| 2016/0296251 A1 | 10/2016 | Olson et al. | |
| 2016/0296252 A1 | 10/2016 | Olson et al. | |
| 2016/0296268 A1 | 10/2016 | Gee et al. | |
| 2016/0302819 A1 | 10/2016 | Stulen et al. | |
| 2016/0374712 A1 | 12/2016 | Stulen et al. | |
| 2017/0095295 A1 | 4/2017 | Overmyer | |
| 2017/0196637 A1 | 7/2017 | Shelton, IV et al. | |
| 2017/0202571 A1 | 7/2017 | Shelton, IV et al. | |
| 2017/0202599 A1 | 7/2017 | Shelton, IV et al. | |
| 2017/0202609 A1 | 7/2017 | Shelton, IV et al. | |
| 2018/0000543 A1 | 1/2018 | Hibner | |
| 2018/0049813 A1 | 2/2018 | Yates et al. | |
| 2019/0021752 A1 | 1/2019 | Boudreaux | |
| 2019/0290318 A1 | 9/2019 | Boudreaux | |

FOREIGN PATENT DOCUMENTS

| | | |
|---|---|---|
| WO | 2003082133 A1 | 10/2003 |
| WO | 2014148898 A1 | 9/2014 |
| WO | 2014151621 A1 | 9/2014 |
| WO | 2014151952 A1 | 9/2014 |
| WO | 2016168184 A1 | 10/2016 |

OTHER PUBLICATIONS

International Search Report and Written Opinion for PCT/US2018/042295 dated Oct. 25, 2018 (15 pages).

International Search Report and Written Opinion for PCT International Application No. PCT/IB2019/055161, dated Nov. 13, 2019 (16 pages).

* cited by examiner

ULTRASONIC TRANSDUCER TO BLADE ACOUSTIC COUPLING, CONNECTIONS, AND CONFIGURATIONS

CROSS-REFERENCE TO RELATED APPLICATIONS

This application is a continuation-in-part of U.S. patent application Ser. No. 15/654,428, filed on Jul. 19, 2017.

TECHNICAL FIELD

The present disclosure generally relates to robotic ultrasonic surgical instruments. In particular, the present disclosures relate to a system for controlling articulation forces in a robotic surgical arm with a surgical end effector.

BACKGROUND

Robotic surgical tools may be useful in providing stable and reliable application for surgical procedures. Various components may be interchangeable such that a single support apparatus may be used to attach to different modular robotic surgical arms. Some of these robotic systems employ multiple motors to control individual components that may move independently but still involve a degree of interrelationship. It is desirable to develop control algorithms to reliably govern the movements of two or more of these components when there is an interrelationship.

In robotic surgery, it is desirable to have an end-effector with six degrees of motion to mimic the surgeon's hands and to better access tissue. Ultrasonic robotic instruments that have an ultrasonic blade can only bend at one point and still have a usable pivot to tip length. This means that the ultrasonic blade cannot rotate distal of the articulation bend.

SUMMARY

In one general aspect, the present disclosure is directed to a surgical instrument, comprising a rotatable shaft comprising an articulation section; an ultrasonic waveguide disposed within the shaft, wherein the ultrasonic waveguide is configured to articulate at the articulation section; and a rotatable clamp arm located distal of the articulation section of the rotatable shaft, wherein the rotatable clamp arm is configured to rotate independently of the rotatable shaft distal of the articulation section.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

DESCRIPTION

Before explaining various aspects in detail, it should be noted that such aspects are not limited in their application or use to the details of construction and arrangement of parts illustrated in the accompanying drawings and description. The illustrative aspects may be implemented or incorporated in other aspects, variations and modifications, and may be practiced or carried out in various ways. For example, the surgical instruments disclosed below are illustrative only and not meant to limit the scope or application thereof. Furthermore, unless otherwise indicated, the terms and expressions employed herein have been chosen for the purpose of describing the illustrative aspects for the convenience of the reader and are not to limit the scope thereof.

Certain aspects will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting aspects and that the scope of the various aspects is defined solely by the claims. The features illustrated or described in connection with one aspect may be combined with the features of other aspects. Such modifications and variations are intended to be included within the scope of the claims.

The present disclosure is directed to various aspects of a robotic ultrasonic surgical instrument with six degrees of freedom. The robotic ultrasonic surgical instrument includes a rotatable shaft, articulatable end effector, and independently rotatable distal clamp arm. In addition, the clamp arm is movable between open and closed positions. The disclosure now turns to the figures where several aspects of a robotic ultrasonic surgical instrument with six degrees of freedom are illustrated.

Figure 1:
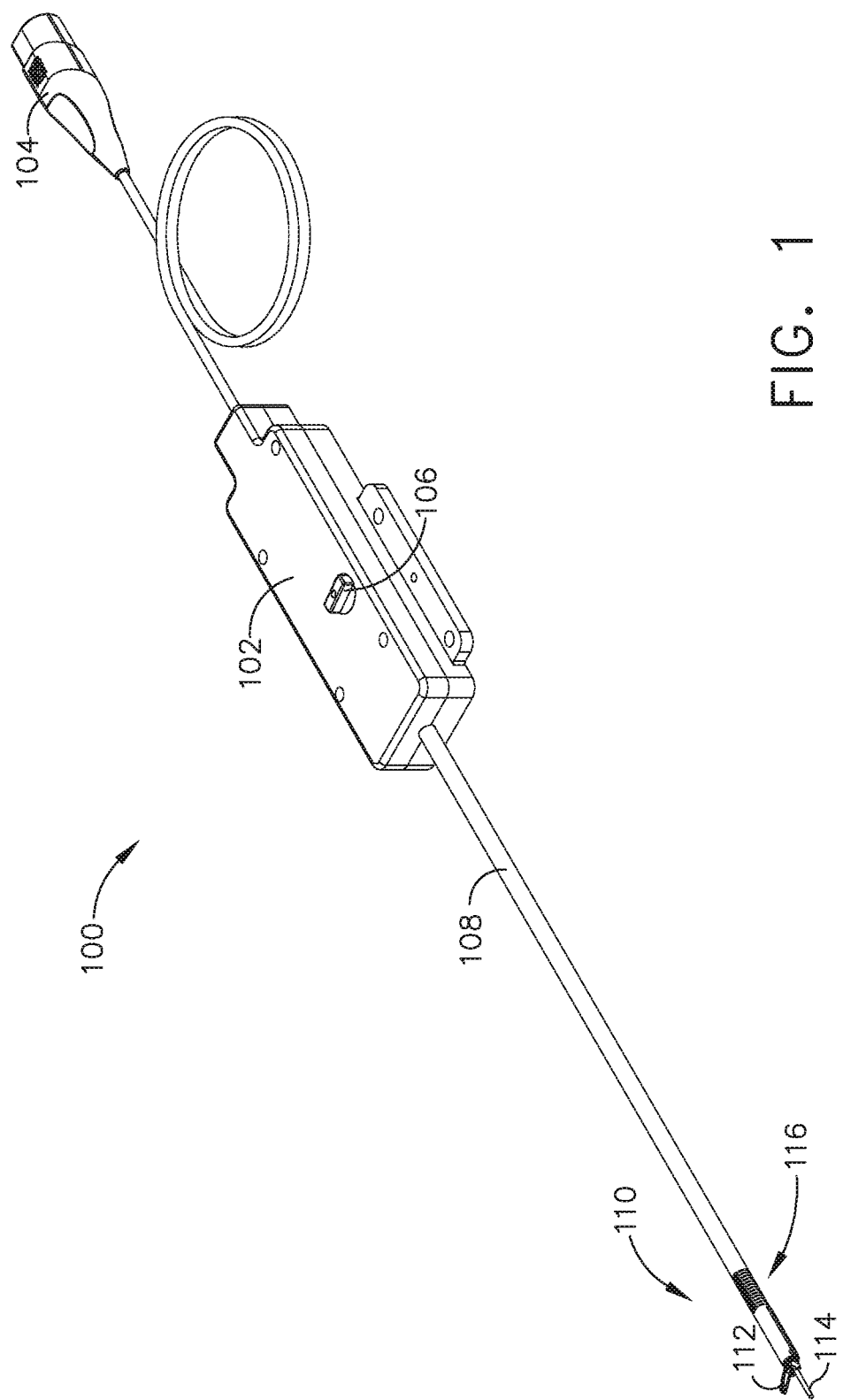
FIG. 1 illustrates a robotic ultrasonic surgical instrument with six degrees of freedom, according to one aspect of this disclosure.
Figure 3:
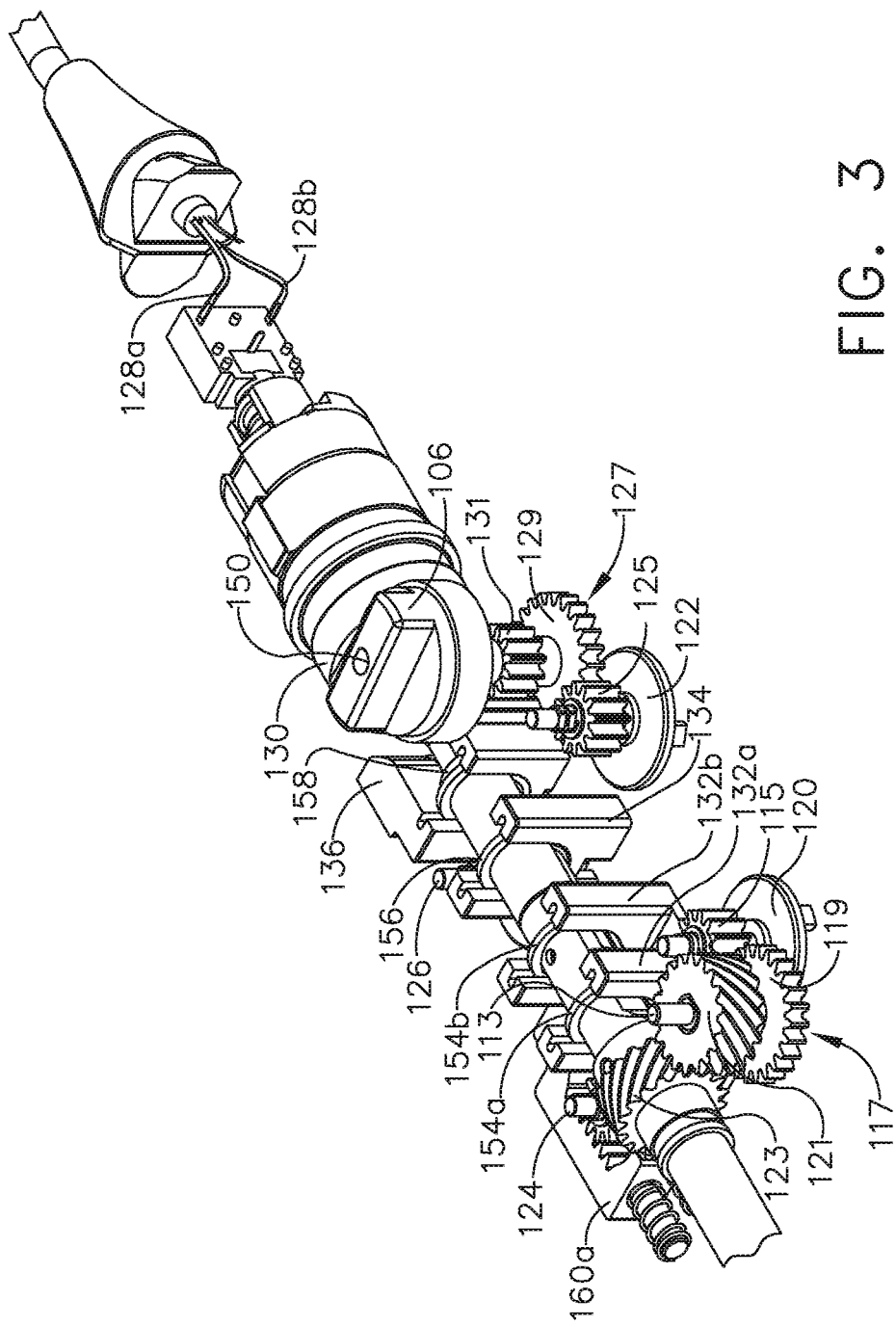
FIG. 3 is a perspective view of the shaft roll, clamp arm closure, articulation, and clamp arm roll gear mechanism, according to one aspect of this disclosure.

FIG. 1 illustrates a robotic ultrasonic surgical instrument 100 with six degrees of freedom, according to one aspect of this disclosure. The surgical instrument 100 includes a robotic interface 102, an ultrasonic energy cord 104, an outer shaft 108, and an end effector 110. The ultrasonic energy cord 104 is configured to electrically couple an ultrasonic energy source to an ultrasonic transducer 130 (FIG. 3) by way of electrically conductive elements 128a, 128b (FIG. 3). The ultrasonic transducer 130 is acoustically coupled to an ultrasonic blade 114. The robotic interface 102 includes a bailout knob 106 configured to enable the clinician to manually take over operation of the robotic ultrasonic surgical instrument 100 should the robotic interface 102 become disabled. The robotic interface 102 is coupled to the outer shaft 108 which is coupled to end effector 110. The end effector 110 includes a clamp arm 112 pivotally coupled to an ultrasonic blade 114. An articulation section 116 enables the end effector 110 to articulate. Throughout the present disclosure, the term "proximal" refers to a location at or near the robotic interface 102 and the term "distal" refers to a location at or near the end effector 110 or the ultrasonic blade 114 tip. Within the robotic interface 102, the term "proximal" refers to the end of the robotic interface 102 where the energy cord 104 is received and the and the term "distal" refers to the end where the outer shaft 108 couples to the robotic interface 102.

In one aspect, the ultrasonic blade 114 may be configured with a straight and uniformly round distal tip so that the clamp arm 112 can rotate about the uniformly round distal tip of the ultrasonic blade 114 and clamp in any orientation of the uniformly round distal tip the ultrasonic blade 114. Rotating the distal tip of the ultrasonic blade 114 distal of the articulation section 116 presents some challenges because the ultrasonic blade 114 takes up most of the space defined within the outer shaft 108 and there is little space available for additional components.

Figure 2:
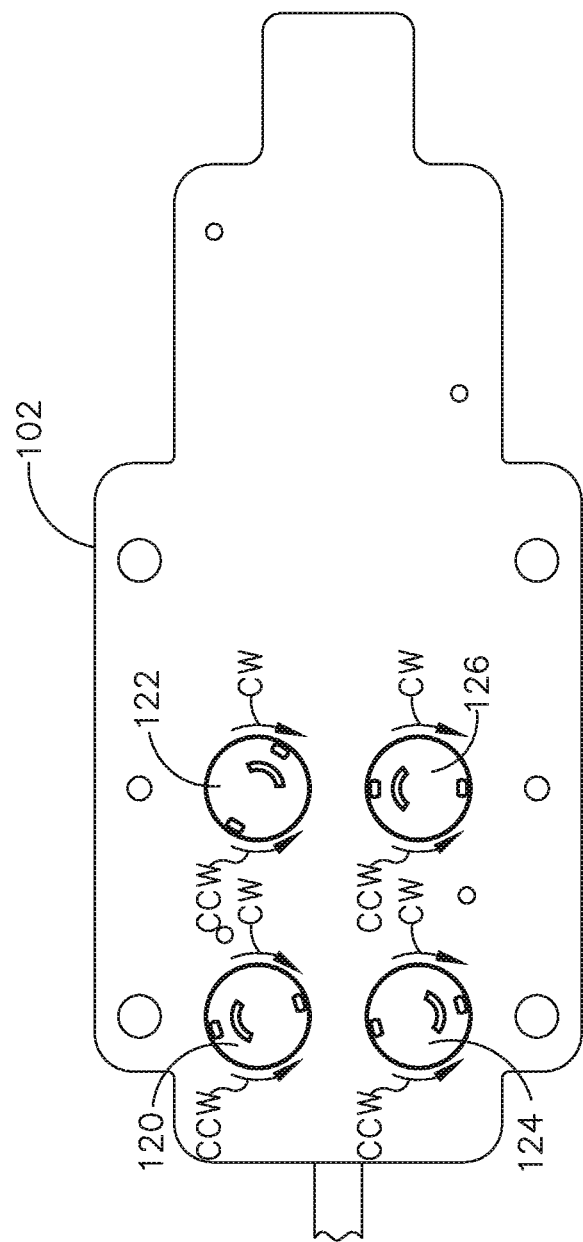
FIG. 2 is a bottom view of the robotic interface showing the rotary input motor interfaces according to one aspect of this disclosure.

FIG. 2 is a bottom view of the robotic interface 102 showing the rotary input motor interfaces according to one aspect of this disclosure. The robotic interface 102 includes four rotary inputs 120, 122, 124, 126 to control various aspects of the robotic ultrasonic surgical instrument 100. The rotary inputs 120, 122, 124, 126 each couple to a separate electric motor controlled by a surgical robot control system. Functions and operations of the robotic ultrasonic surgical instrument 100 are derived from the four rotary inputs 120, 122, 124, 126. The rotary motions of the four rotary inputs 120, 122, 124, 126 enable the robotic ultrasonic surgical instrument 100 to have six degrees of freedom.

A shaft roll rotary input 120 is configured to couple to a shaft roll motor controlled by a surgical robot control system. The shaft roll motor rotates the shaft roll rotary input 120 in either direction (clockwise or counterclockwise) to rotate the outer shaft 108. The robotic interface 102 converts the rotary motion of the shaft roll rotary input 120 to a rotary motion of the outer shaft 108. The direction of rotation of the shaft 108 is based on the direction of rotation of the shaft roll rotary input 120. The direction of rotation of the outer shaft 108 may or may not correspond to the direction of rotation of the shaft roll rotary input 120. In the present disclosure, rotation of the shaft roll rotary input 120 will be referenced as clockwise (CW) and counterclockwise (CCW) relative to the bottom of the robotic interface 102 shown in FIG. 2 where the shaft roll rotary input 120 couples to the motor.

A clamp arm closure rotary input 122 is configured to couple to a clamp arm closure motor controlled by the surgical robot control system. The clamp arm closure motor rotates the clamp arm closure rotary input 122 in either direction to close and open the clamp arm 112. The robotic interface 102 converts the rotary motion of the clamp arm closure rotary input 122 to a motion to close or open the clamp arm 112 relative to the ultrasonic blade 114 based on the direction of rotation of the clamp arm closure rotary input 122. In the present disclosure, rotation of the clamp arm closure rotary input 122 will be referenced as clockwise (CW) and counterclockwise (CCW) relative to the bottom of the robotic interface 102 shown in FIG. 2 where the clamp arm closure rotary input 122 couples to the motor.

An articulation rotary input 124 is configured to couple to an articulation motor controlled by the surgical robot control system. The articulation motor rotates the articulation rotary input 124 in either direction to articulate the end effector 110 left or right at the articulation section 116. The robotic interface 102 converts the rotary motion of the articulation rotary input 124 to a left/right articulation motion of the end effector 110 based on the direction of rotation of the articulation rotary input 124. In the present disclosure, rotation of the articulation rotary input 124 will be referenced as clockwise (CW) and counterclockwise (CCW) relative to the bottom of the robotic interface 102 shown in FIG. 2 where the articulation rotary input 124 couples to the motor. In one aspect, the articulation section 116 can articulate over a range of ±65°, for example.

A clamp arm roll rotary input 126 is configured to couple to a clamp arm roll motor controlled by the surgical robot control system. The clamp arm roll motor rotates the clamp arm roll rotary input 126 in either direction to rotate the clamp arm 112 portion of the end effector 110 about the ultrasonic blade 114. The robotic interface 102 converts the rotary motion of the clamp arm roll rotary input 126 to a clockwise/counterclockwise rotation motion of the clamp arm 112 based on the direction of rotation of the clamp arm roll rotary input 126. In the present disclosure, rotation of the clamp arm roll rotary input 126 will be referenced as clockwise (CW) and counterclockwise (CCW) relative to the bottom of the robotic interface 102 shown in FIG. 2 where the clamp arm roll rotary input 126 couples to the motor.

Figure 4:
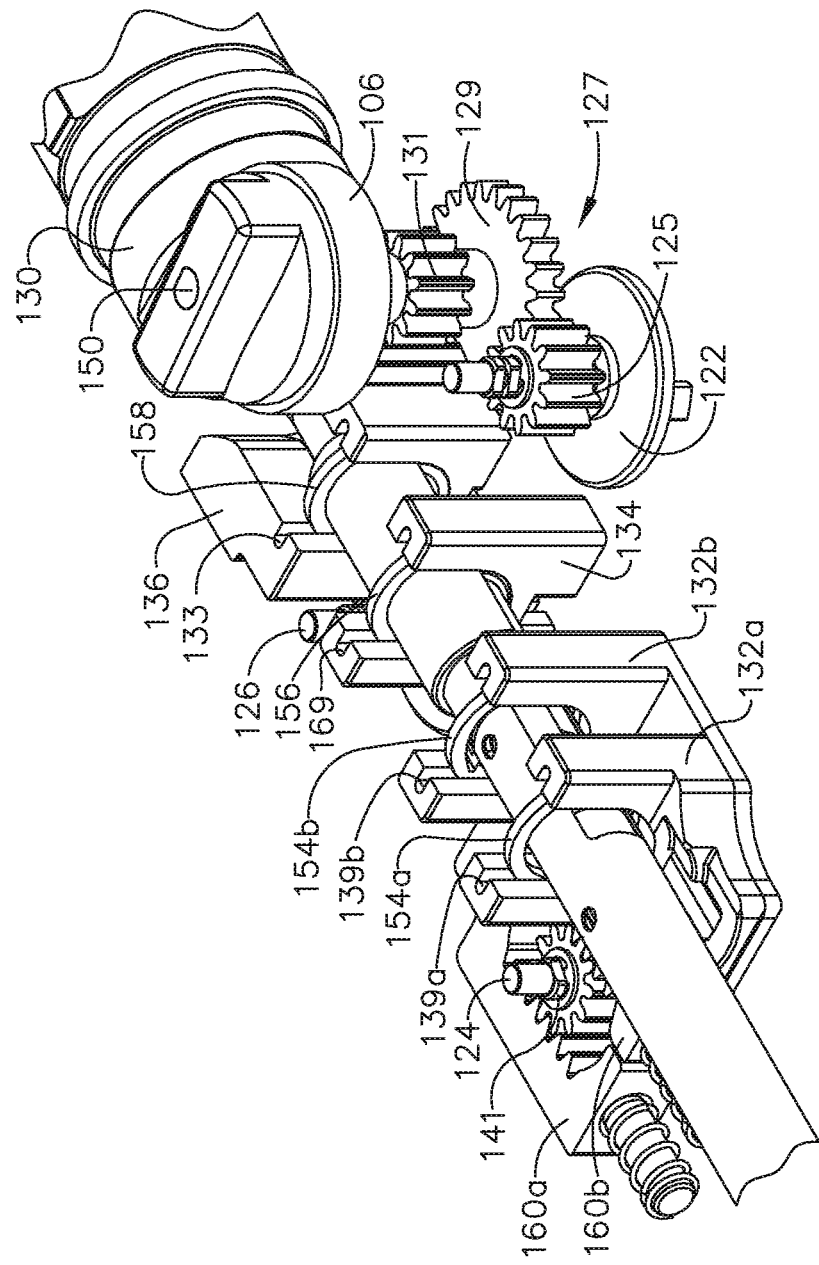
FIG. 4 is a perspective view of the clamp arm closure, articulation, and clamp arm roll gear mechanism, according to one aspect of this disclosure.
Figure 5:
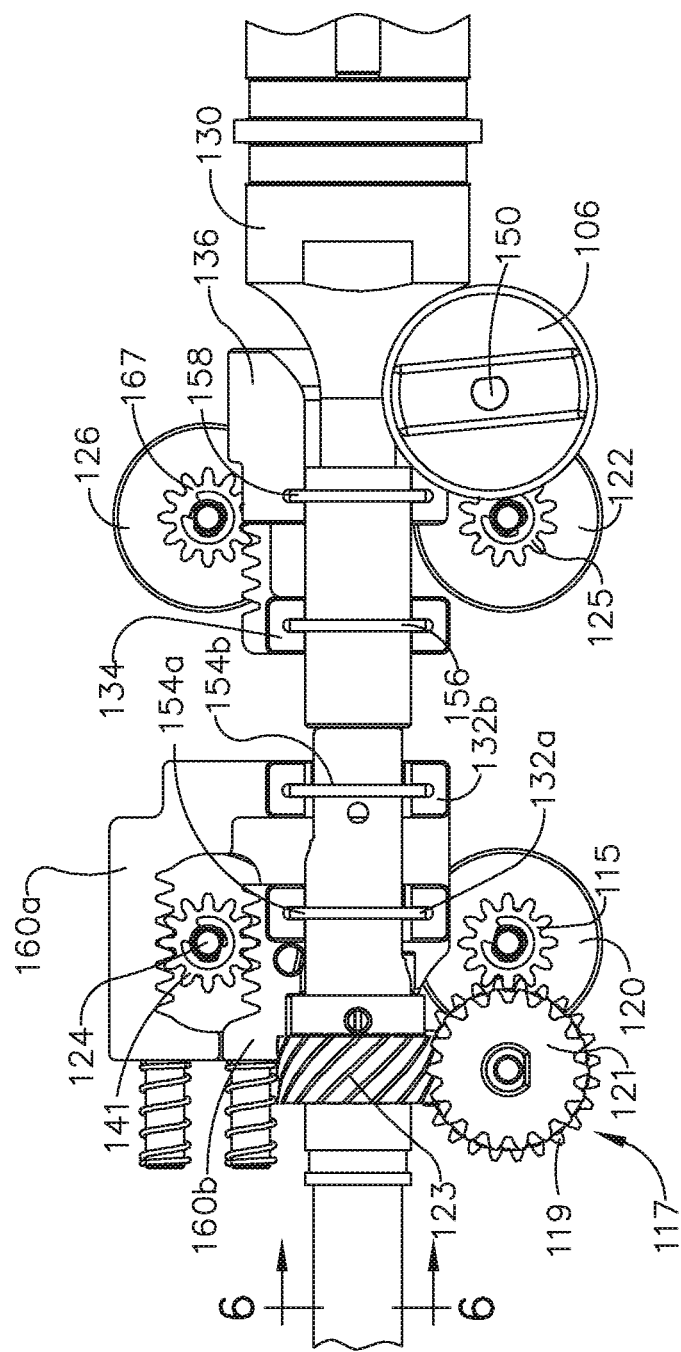
FIG. 5 is a top view of the shaft roll, clamp arm closure, articulation, and clamp arm roll gear mechanism, according to one aspect of this disclosure.

FIGS. 3-5 illustrate the mechanisms within the robotic interface 102 that convert the rotary motion of the shaft roll rotary input 120, the clamp arm closure rotary input 122, the articulation rotary input 124, and clamp arm roll rotary input 126 into shaft roll, clamp arm closure, articulation, and clamp arm roll, respectively, according to one aspect of this disclosure. FIG. 3 is a perspective view of the shaft roll, clamp arm closure, articulation, and clamp arm roll gear mechanism, according to one aspect of this disclosure. FIG. 3 illustrates a gear assembly 117 that includes a first helical gear 121 that cooperates with a second cross axis helical gear 123 to rotate the outer shaft 108. Also shown in FIG. 3 are the electrically conductive elements 128a, 128b apply electrical energy from an ultrasonic generator to the ultrasonic transducer 130. The ultrasonic transducer 130 converts the electrical energy into ultrasonic mechanical vibrations to drive the ultrasonic blade 114. FIG. 4 is a perspective view of the clamp arm closure, articulation, and clamp arm roll gear mechanism, according to one aspect of this disclosure. In FIG. 4, the gear assembly 117 and the first and second helical gears 121, 123 are omitted to provide a view of the articulation mechanism. FIG. 5 is a top view of the shaft roll, clamp arm closure, articulation, and clamp arm roll gear mechanism, according to one aspect of this disclosure. The mechanisms illustrated in FIGS. 3-5 are further described hereinbelow.

Figure 6:
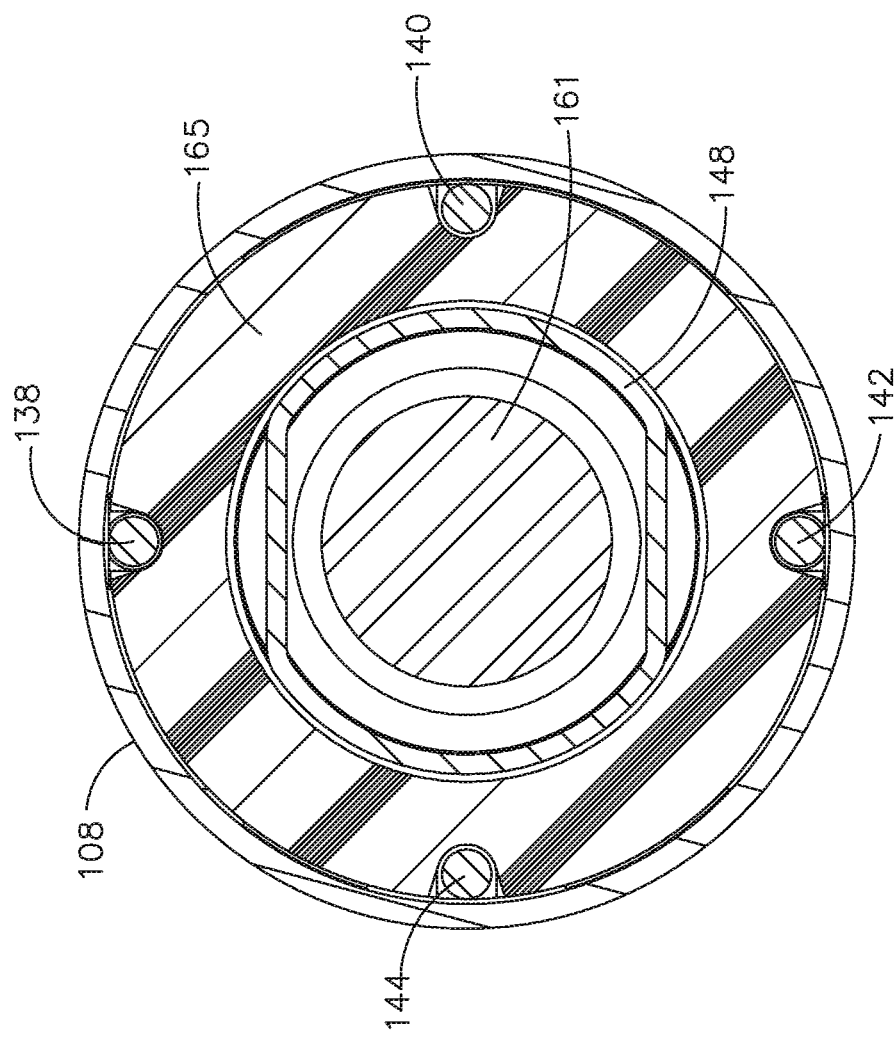
FIG. 6 is a section view of the shaft portion of the robotic ultrasonic surgical instrument taken at section 6-6 shown in FIG. 5, according to one aspect of this disclosure.

FIG. 6 is a section view of the shaft portion of the robotic ultrasonic surgical instrument 100 taken at section 6-6 shown in FIG. 5, according to one aspect of this disclosure. As shown, the outer shaft 108 surrounds an extruded guide 165, an overmold 148, and an ultrasonic waveguide 161. The mechanism in accordance with this disclosure employs four rods that are distributed to the sides, top, and bottom of the ultrasonic waveguide 161. The extruded overmold defines longitudinal grooves or channels to receive a clamp arm closure rod 138, left and right articulation rods 140, 144, and a clamp arm roll rod 142.

Figure 18:
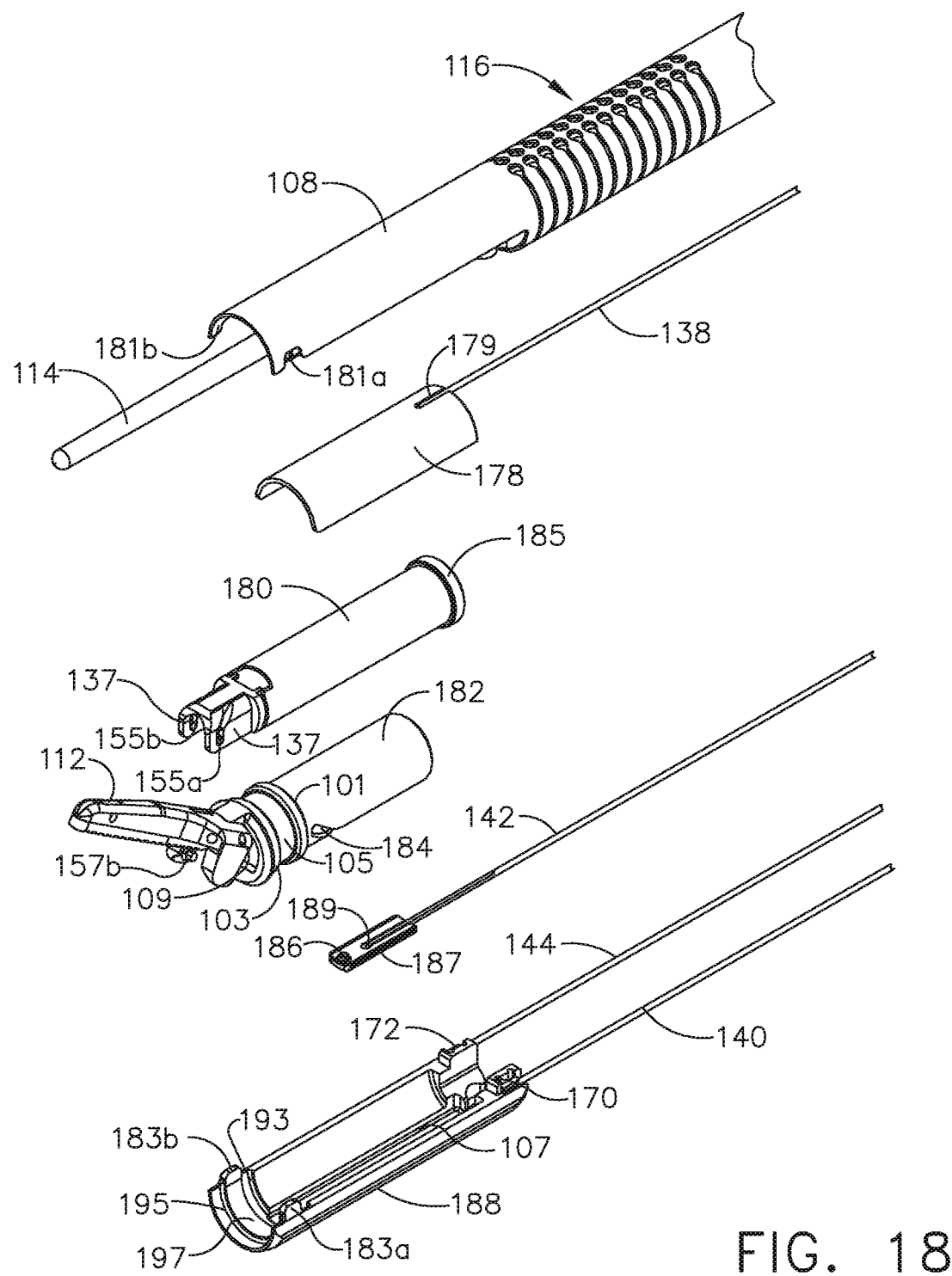
FIG. 18 is an exploded view of a distal portion of the robotic ultrasonic surgical instrument shown in FIG. 1 comprising a spiral slotted mechanism, according to one aspect of this disclosure.

With reference now also to FIG. 18, the clamp arm closure rod 138 is located above the ultrasonic waveguide 161 and is attached to a coupler 178 at connection 179. The coupler 178 is rotationally fitted to a rotatable clamp arm closure tube 180. The coupler 178 moves back (proximally) and forth (distally) but does not rotate. The rotatable clamp arm closure tube 180 can rotate in the coupler 178. Pulling the clamp arm closure rod 138 proximally closes the clamp arm 112 and pushing on the clamp arm closure rod 138 distally opens the clamp arm 112.

The left and right articulation rods 140, 144 on either side of the ultrasonic waveguide 161 are attached to the shaft 108 distal of the articulation section 116, respectively. As shown in FIG. 18, in one aspect, the left and right articulation rods 140, 144 are attached to a clamp arm cap 188 at connections 170, 172, respectively. The clamp arm cap 188 is attached to the shaft 108 by tabs 183a, 183b that are received in notches 181a, 181b defined by the shaft 108. Pulling on the left articulation rod 140 and pushing the right articulation rod 144 articulates the end effector 110 to the left at the articulation section 116 and thus articulates the ultrasonic blade 114 to the left. Pulling the right articulation rod 144 and pushing on the left articulation rod 140 articulates the end effector 110 to the right at the articulation section 116 and thus articulates the ultrasonic blade 114 to the right.

Finally, in one aspect, as shown in FIG. 18, the clamp arm roll rod 142 is attached to a spiral slot pin roll rod coupler 187 at connection 189. The spiral slot pin roll rod coupler 187 includes a clamp arm roll pin 186 that is slidably received in a spiral slot 184 defined in a spiral slotted clamp arm roll tube 182 that is attached to the clamp arm 112, thus enabling the clamp arm 112 to freely rotate. Moving the clamp arm roll pin 186 back (proximally) and forth (distally) in the spiral slot 184 rotates the clamp arm 112 and the rotatable clamp arm closure tube 180 relative to the shaft 108. The clamp arm roll pin 186 in the spiral slot 184 mechanism provides a smooth continuous motion to the clamp arm 112 with infinite stop points. Pulling proximally on the clamp arm roll rod 142 connected to the clamp arm roll pin 186 rotates the clamp arm one direction and pushing distally on the clamp arm roll rod 142 rotates it the opposite direction. The clamp arm closure rod 138 and the clamp arm roll rod 142 travel along the top and bottom center of the shaft 108. This location subjects these rods 138, 142 to minimal length change when articulated so that the end effector 110 does not rotate and the clamp arm 112 does not close when the device articulates.

As described herein, connections 179, 189, 170, 172 shown in FIG. 18 may be implemented in any suitable fashion. For example, the connections 179, 189, 170, 172 may be made by clevis and pin, solder, weld, threads (male or female), press fit, crimp, swage, rivet, epoxy, or any combinations thereof. The rods 138, 140, 142, 144 can be made of any suitable metal, plastic, or composite material that includes one of a metal, plastic, or carbon material. The rods 138, 140, 142, 144 should have a stiffness or rigidity suitable to withstand the pulling and pushing forces suitable for closing and opening the clamp arm 112, articulating the end effector 110 in the left and right directions at the articulation section 116, and rotating the clamp arm 112 distal of the articulation section 116, while having enough flexibility to move around the articulated articulation section 116 in the articulated configuration.

Figure 10:
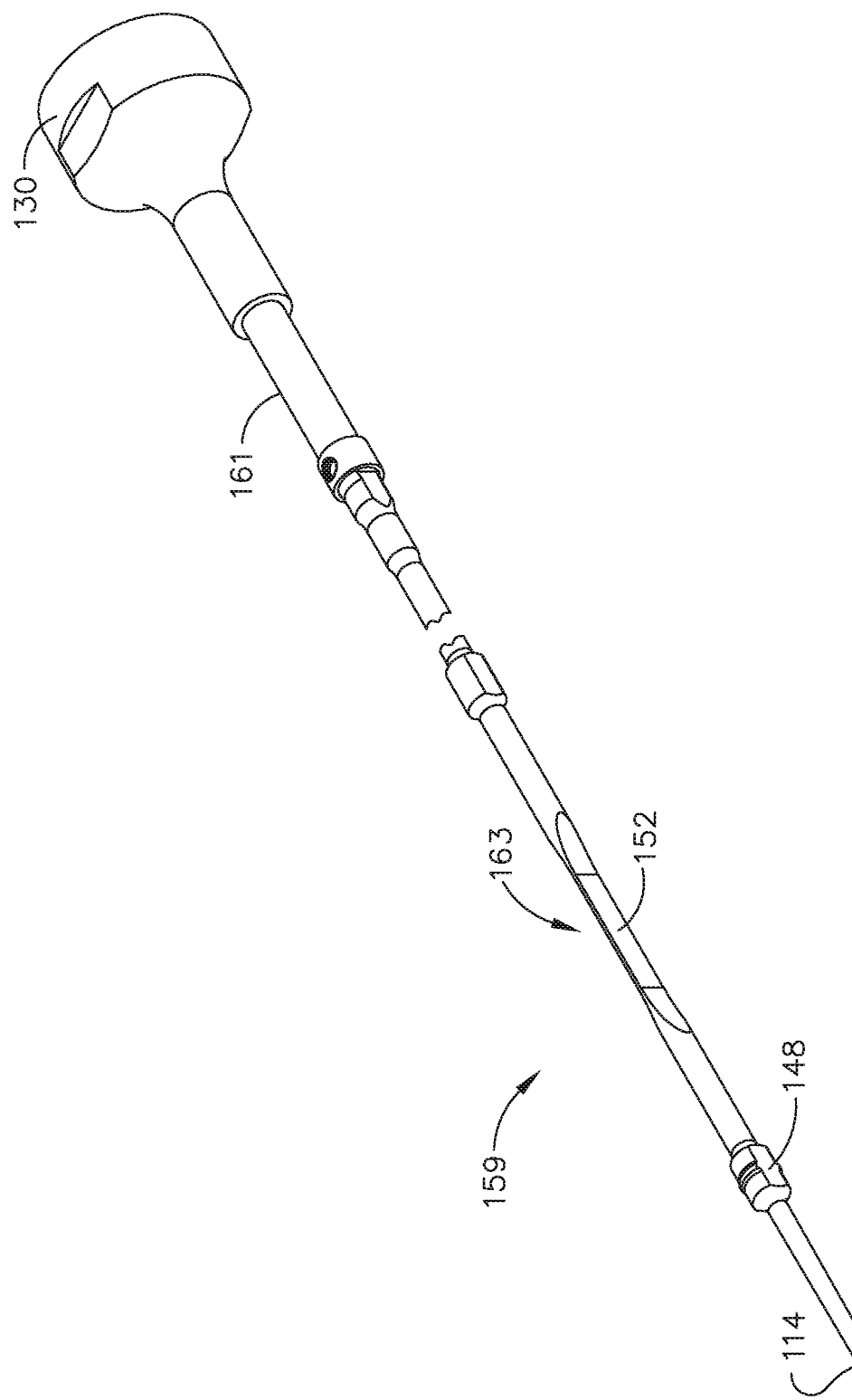
FIG. 10 illustrates an ultrasonic system, according to one aspect of this disclosure.
Figure 11:
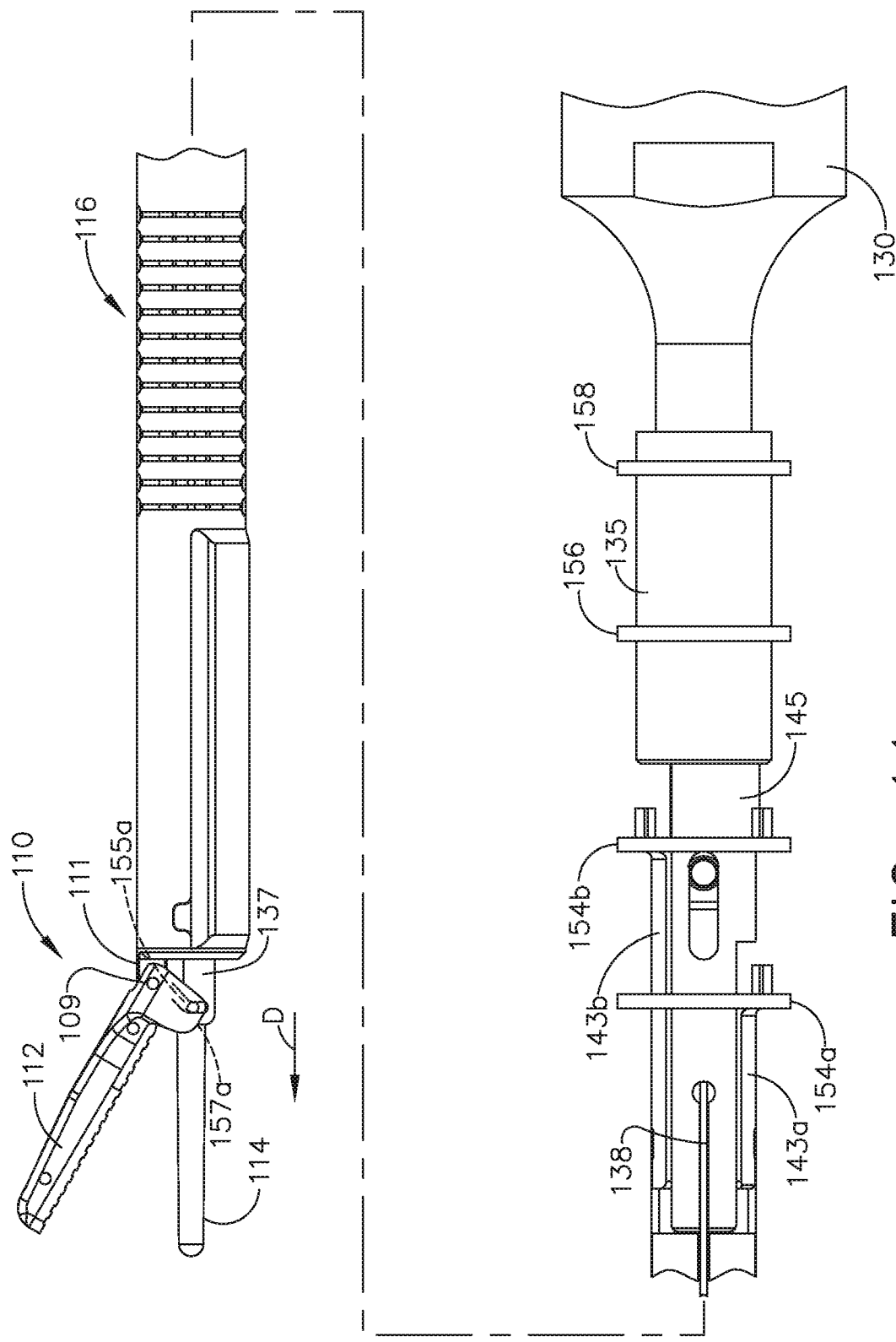
FIG. 11 is an elevation view of the surgical instrument shown in FIG. 1 with the clamp arm in an open position, according to one aspect of this disclosure.
Figure 12:
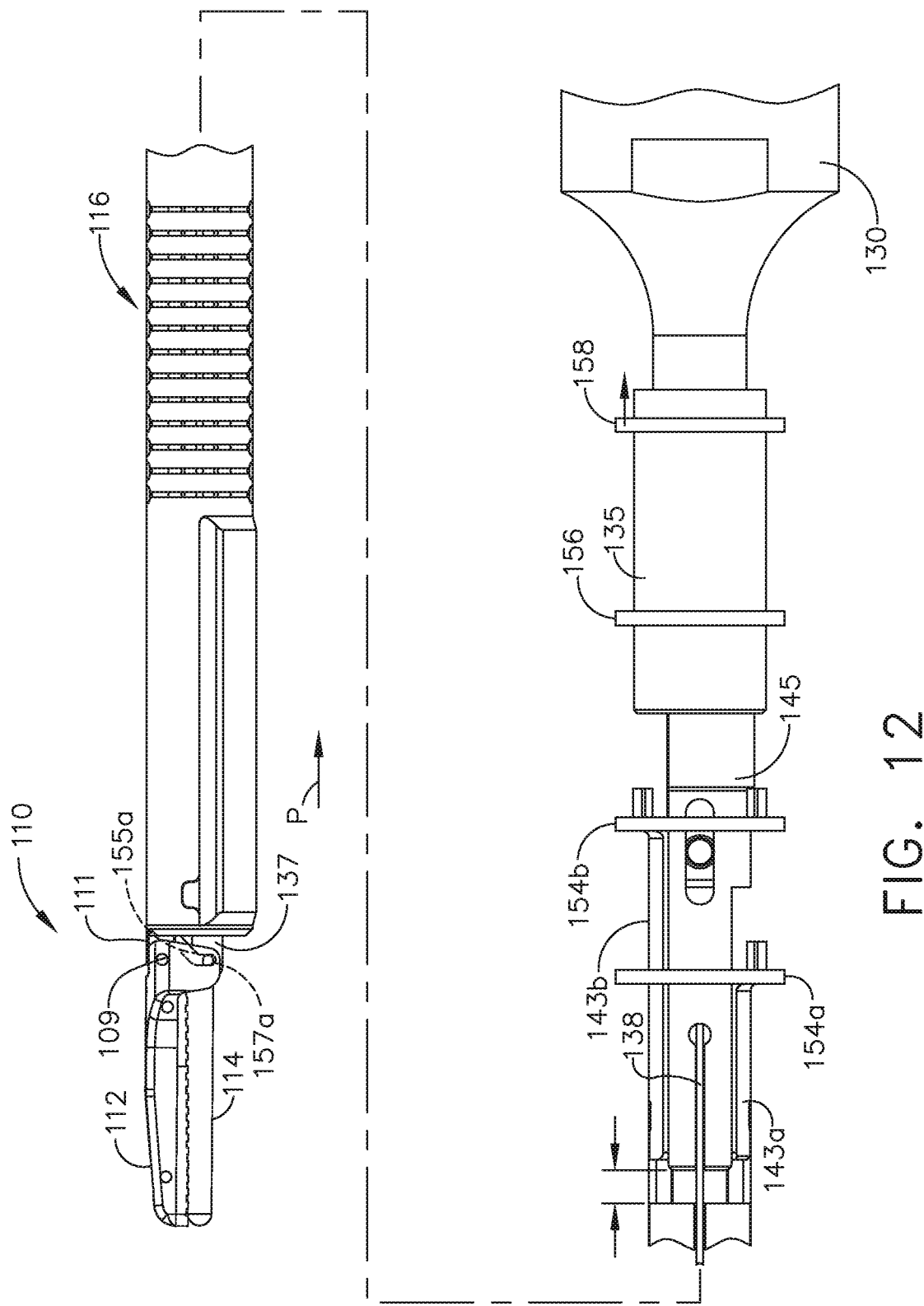
FIG. 12 is an elevation view of the surgical instrument shown in FIG. 1 with the clamp arm in a closed position, according to one aspect of this disclosure.

FIG. 10 illustrates an ultrasonic system 159 according to one aspect of this disclosure. The ultrasonic system 159 includes an ultrasonic transducer 130, and ultrasonic blade 114, and an ultrasonic transmission waveguide 161 that acoustically couples the ultrasonic transducer 130 to the ultrasonic blade 114. Ultrasonic vibrations are generated by the ultrasonic transducer 130 when energized by a suitable electrical energy signal. The ultrasonic vibrations generated by the ultrasonic transducer 130 are transmitted to the ultrasonic blade 114 by the ultrasonic transmission waveguide 161. The ultrasonic transmission waveguide 161 may be a single unitary component or may include multiple components attached together by welded, threaded, or fitted connection. The ultrasonic waveguide 161 includes a thin walled section 152 defining an articulation section 163 to enable the end effector 110 to articulate in left and right directions as described herein about the articulation section 163. The ultrasonic vibrations transmitted to the ultrasonic blade 114 are transmitted to organic tissue at suitable energy levels and using a suitable end effector 110, which may or may not include a clamp arm 112, may be used to cut, dissect, elevate or cauterize tissue or to separate muscle tissue from bone. Ultrasonic instruments utilizing solid core technology are particularly advantageous because of the amount of ultrasonic energy that may be transmitted from the ultrasonic transducer 130, through the waveguide 161, to the ultrasonic blade 114. In one aspect, the ultrasonic blade 114 tip is partially round for a certain amount of degrees and defines a cutting portion at a bottom portion of the ultrasonic blade 114.

Activating or exciting the ultrasonic blade 114 at ultrasonic frequencies induces longitudinal vibratory movement that generates localized heat within adjacent tissue. Because of the nature of ultrasonic instruments, a particular ultrasonically actuated ultrasonic blade 114 may be designed to perform numerous functions, including, for example, cutting and coagulation. These surgical effects may be enhanced by incorporating the clamp arm 112 to apply pressure to the tissue during the procedure. The clamp arm 112 may include a lubricious pad to further enhance the surgical effects. Ultrasonic vibration is induced in the ultrasonic blade 114 by electrically exciting the ultrasonic transducer 130, for example. The transducer 130 may be constructed of one or more piezoelectric or magnetostrictive elements in the instrument hand piece. Vibrations generated by the transducer 130 are transmitted to the ultrasonic blade 114 via the ultrasonic waveguide 161 extending from the transducer 130 to the ultrasonic blade 114 located in the end effector 110. The waveguide 161 and the ultrasonic blade 114 are designed to resonate at the same frequency as the transducer 130. Therefore, when the ultrasonic blade 114 is attached to the transducer 130, the overall system frequency is the same as the vibratory frequency of the transducer 130 itself.

The amplitude of the longitudinal ultrasonic vibration at the tip, d, of the ultrasonic blade 114 behaves as a simple sinusoid at the resonant frequency as given by:

$$d = A \sin(\omega t)$$

where:

$\omega$=the radian frequency which equals $2\pi$ times the cyclic frequency, f; and A=the zero-to-peak amplitude.

The longitudinal excursion of the distal tip of the ultrasonic blade 114 is defined as the peak-to-peak (p-t-p) amplitude, which is just twice the amplitude of the sine wave or 2A. Often, the ultrasonic blade 114, owing to the longitudinal excursion, can cut and/or coagulate tissue.

Outer Shaft Rotation

In one aspect, the present disclosure provides a mechanism to rotate the outer shaft 108 of the robotic ultrasonic surgical instrument 100 in a clockwise or counterclockwise direction. Accordingly, with reference now to FIGS. 2-6, the shaft roll rotary input 120 includes a drive gear 115 which is coupled to a gear assembly 117. As shown particularly in FIG. 6, the gear assembly 117 includes a driven gear 119 which rotates a shaft 113. A first helical gear 121 is attached to the shaft 113 and rotates with the driven gear 119. The first helical gear 121 drives a second cross axis helical gear 123 attached about the outer shaft 108 to rotate the outer shaft 108. The direction of rotation of the outer shaft 108 depends on the direction of rotation of the shaft roll rotary input 120. In the illustrated example, a CW rotation of the shaft roll rotary input 120 as described in FIG. 2 produces a corresponding CW rotation of the outer shaft 108 and a CCW rotation of the shaft roll rotary input 120 as described in FIG. 2 produces a corresponding CCW rotation of the outer shaft 108.

Clamp Arm Open and Closure

Figure 8:
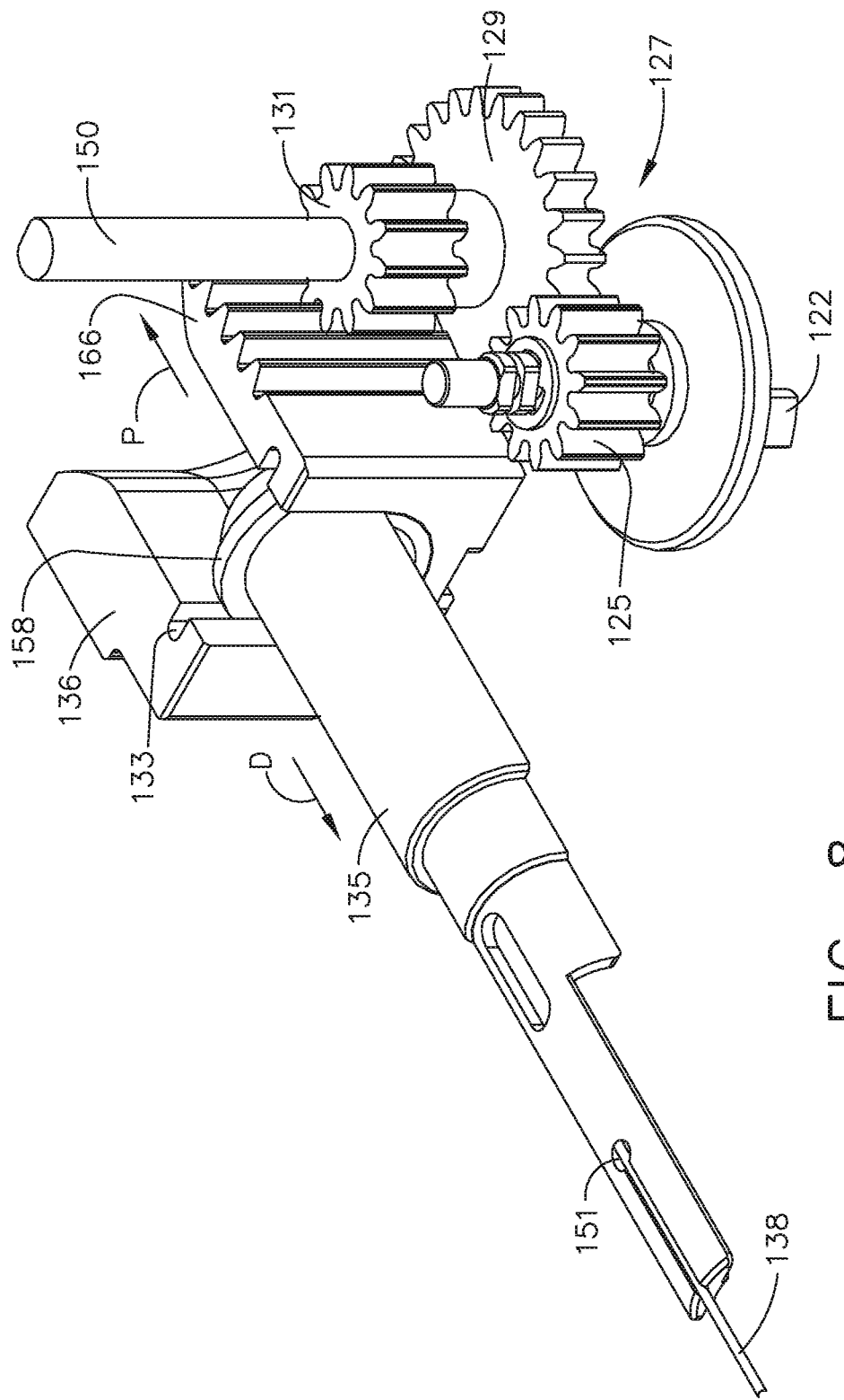
FIG. 8 is a perspective view of a clamp arm closure rotary input interface and drive section, according to one aspect of this disclosure.

In one aspect, the present disclosure provides a mechanism to open and close the clamp arm 112. Accordingly, with reference now generally to FIGS. 2-6, 8, 11, 12, and 18, and in particular to FIG. 8, that shows a perspective view of a clamp arm closure rotary input interface and drive section, according to one aspect of this disclosure. As shown in FIG. 8, the clamp arm closure rotary input 122 includes a drive gear 125 coupled to a gear assembly 127. The gear assembly 127 includes a pinion gear 129 to drive a clamp arm closure rack gear 166. The clamp arm closure rack gear 166 includes a rack 136 that defines a semiannular groove 133 to receive a clamp arm closure ring 158. The clamp arm closure ring 158 is attached to a closure tube section 135. The closure tube section 135 is attached to a clamp arm closure rod 138 at a connection 151. The connection 151 may be implemented in any suitable fashion, such as, for example, clevis and pin, solder, weld, threads (male or female), press fit, crimp, swage, rivet, epoxy, or any combinations thereof.

Turning briefly to FIG. 18, the clamp arm closure rod 138 is attached to the clamp arm closure coupler 178 that is rotationally fitted to the rotatable clamp arm closure tube 180. The clamp arm closure coupler 178 cooperates with a rotatable clamp arm closure tube 180 to open and close the clamp arm 112. The rotatable clamp arm closure tube 180 includes a closure link 137 that defines slots 155a, 155b on opposite sides of the closure link 137. The slots 155a, 155b engage corresponding pins 157a, 157b formed on the clamp arm 112. The clamp arm closure coupler 178 moves back and forth but does not rotate. The rotatable clamp arm closure tube 180 can rotate in the clamp arm closure coupler 178. Applying a pulling force on the clamp arm closure rod 138 in the proximal direction closes the clamp arm 112 and applying a pushing force on the clamp arm closure rod 138 in a distal direction opens the clamp arm 112.

To close the clamp arm 112, the clamp arm closure rotary input 122 is rotated in a CW direction as described in FIG. 2. The drive gear 125 drives the pinion gear 129 causing the clamp arm closure rack gear 166 and the clamp arm closure ring 158 to translate in the proximal direction P. Accordingly, the clamp arm closure ring 158 pulls the closure tube section 135 and the clamp arm closure rod 138 in the proximal direction P. As the clamp arm closure rod 138 pulls the clamp arm closure coupler 178 in the proximal direction P, the rotatable clamp arm closure tube 180 is pulled in the proximal direction P and the clamp arm pins 157a, 157b engage the corresponding slots 155a, 155b defined by the closure link 137 to rotate the clamp arm 112 from the open position shown in FIG. 11 to the closed position shown in FIG. 12.

To open the clamp arm 112, the clamp arm closure rotary input 122 is rotated in a CCW direction as described in FIG. 2. The drive gear 125 drives the pinion gear 129 causing the clamp arm closure rack gear 166 and the clamp arm closure ring 158 to translate in the distal direction D. Accordingly, the clamp arm closure ring 158 pushes the closure tube section 135 and the clamp arm closure rod 138 in the distal direction D. As the clamp arm closure rod 138 pushes the clamp arm closure coupler 178 in the distal direction D, the rotatable clamp arm closure tube 180 is pushed in the distal direction D and once again the clamp arm pins 157a, 157b engage the corresponding slots 155a, 155b defined by the closure link 137 to rotate the clamp arm 112 from the closed position shown in FIG. 12 to the open position shown in FIG. 11.

The gear assembly 127 includes another gear coupled to the shaft of the bailout knob 106. The gear 131 rotates with the shaft 150. Thus, if there is a malfunction of the robotic interface 102, the clamp arm 112 can be closed or opened manually by rotating the bailout knob 106 CW or CCW, respectively.

End Effector Articulation

In one aspect, the present disclosure provides a mechanism to articulate the end effector 110 left or right at the articulation section 116. Left and right articulation rods 140, 144 positioned on either side of the ultrasonic waveguide 161 are attached to the shaft 108 distal of the articulation section 116. Pulling one articulation rod 140, 144 and pushing the other articulation rod 144, 140 articulates the end effector 110, and thus articulates the ultrasonic blade 114.

Figure 7:
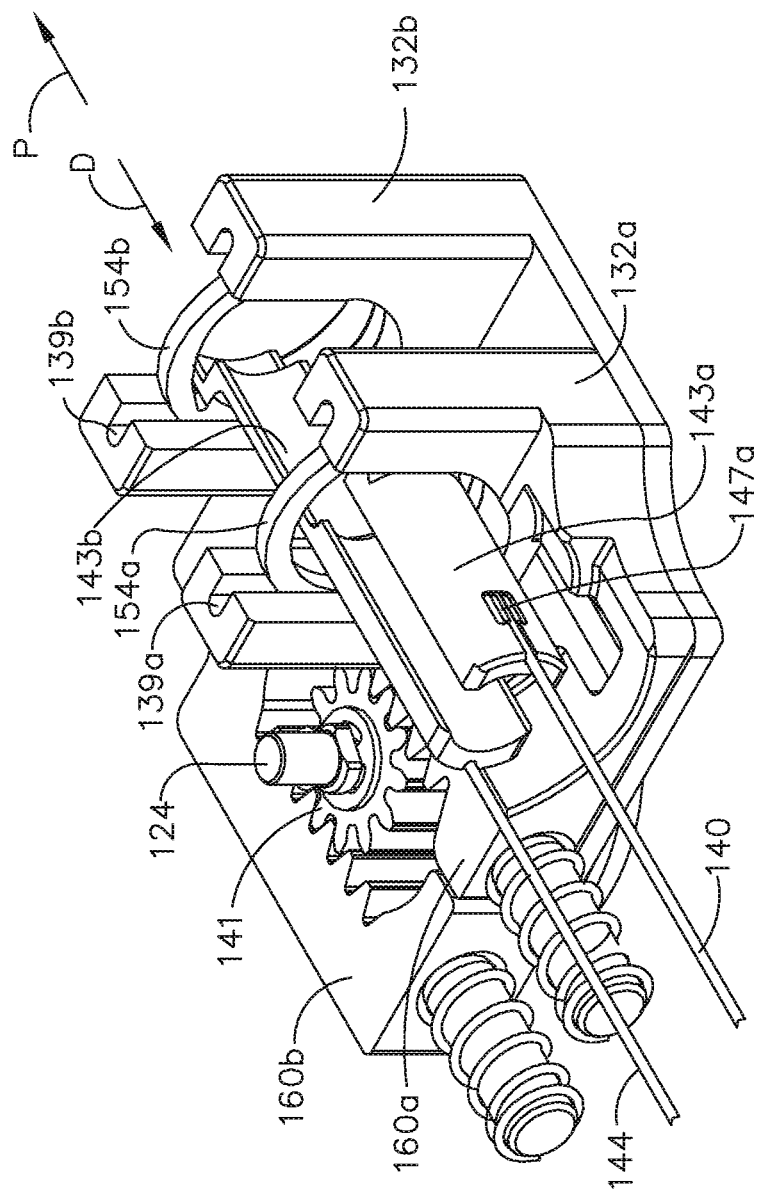
FIG. 7 is a perspective view of an articulation rotary input interface and drive section, according to one aspect of this disclosure.

With reference now generally to FIGS. 2-7, 13, 14, 17, and 18, and in particular to FIG. 7, that shows a perspective view of an articulation rotary input interface and drive section, according to one aspect of this disclosure. As shown in FIG. 7, the articulation rotary input 124 includes a pinion gear 141 that engages first and second articulation rack gears 160a, 160b. The first articulation rack gear 160a includes a first rack 132a that defines a first semiannular groove 139a to receive a first ring 154a. The first ring 154a is attached to a left articulation tube section 143a which is attached to the left articulation rod 140 at a connection 147a. The left articulation rod 140 is attached to a left articulation connection 170 at a distal end of the articulation section 116 (see FIG. 17) and a proximal end of the clamp arm cap 188 (see FIG. 18). The second articulation rack gear 160b includes a second rack 132b that defines a second semiannular groove 139b to receive a second ring 154b. The second ring 154b is attached to a right articulation tube section 143b which is attached to the left articulation rod 140 at a connection similar to connection 147a. The right articulation rod 144 is attached to a right articulation connection 172 at a distal end of the articulation section 116 (see FIG. 17) and a proximal end of the clamp arm cap 188 (see FIG. 18). The connection 147a may be implemented in any suitable fashion, such as, for example, clevis and pin, solder, weld, threads (male or female), press fit, crimp, swage, rivet, epoxy, or any combinations thereof. An outer articulation tube 174 facilitates articulation at the articulation section 116.

Figure 13:
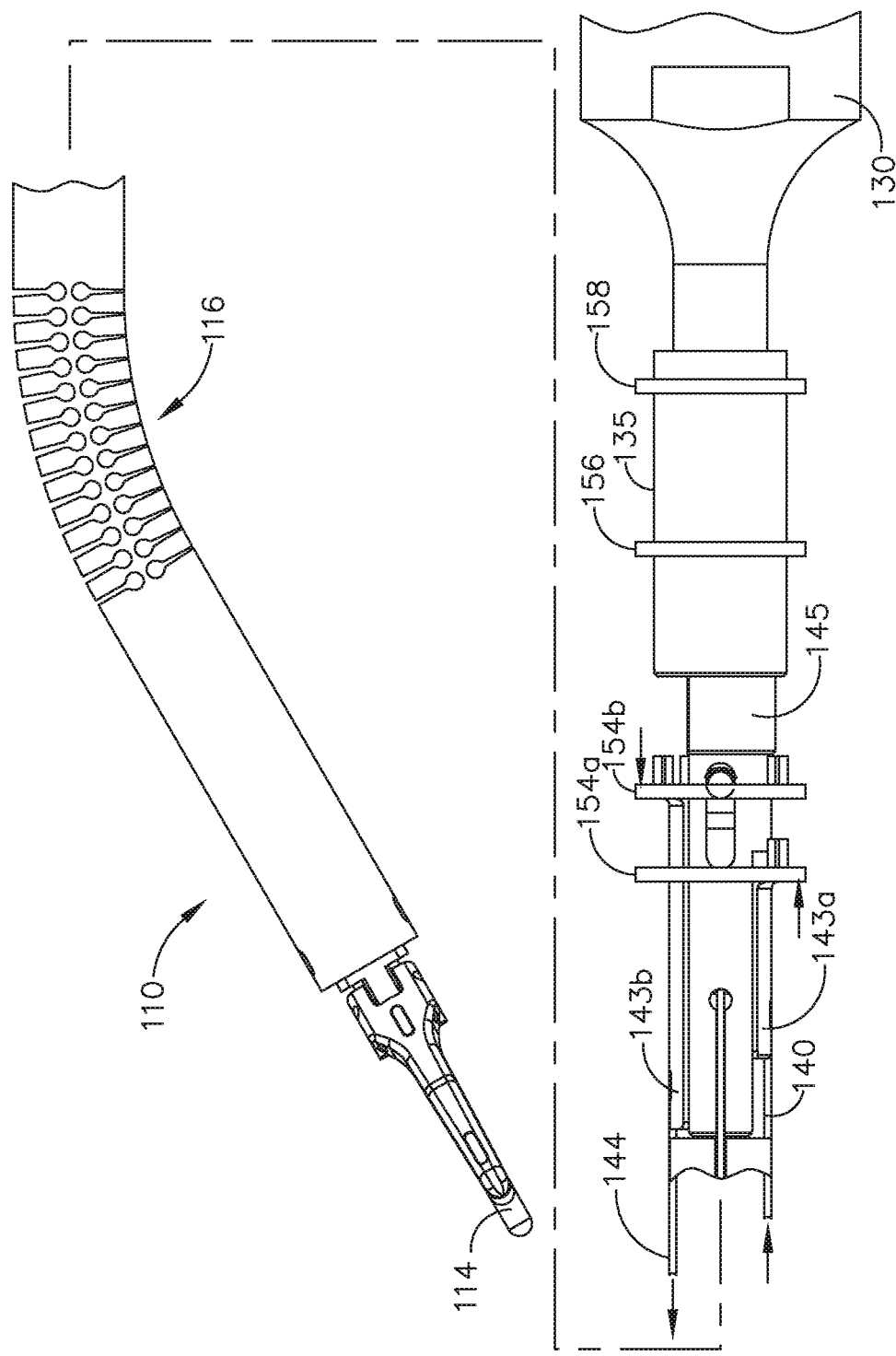
FIG. 13 is a top view of the surgical instrument shown in FIG. 1 with the end effector in a left articulated configuration, according to one aspect of this disclosure.

To articulate the end effector 110 to the left, as shown in FIG. 13, the articulation rotary input 124 is rotated CW as described in FIG. 2. As the articulation rotary input 124 rotates CW, the pinion gear 141 simultaneously drives the first articulation rack gear 160a in the proximal direction P and drives the second articulation rack gear 162b in the distal direction D. In the illustrated example, the first and second racks 132a, 132b are formed integrally, or are fixedly attached to move in unison, with the first and second articulation rack gears 160a, 160b. The first and second racks 132a, 132b move in the same direction as the first and second articulation rack gears 160a, 160b, respectively. The first and second rings 154a, 154b also move in the same direction as the first and second racks 132a, 132b, respectively. Accordingly, the left articulation tube section 143a pulls the left articulation rod 140 in the proximal direction P and the right articulation tube section 143b pushes the left articulation rod 140 in the distal direction D to articulate the end effector 110 to the left as shown in FIG. 13.

Figure 14:
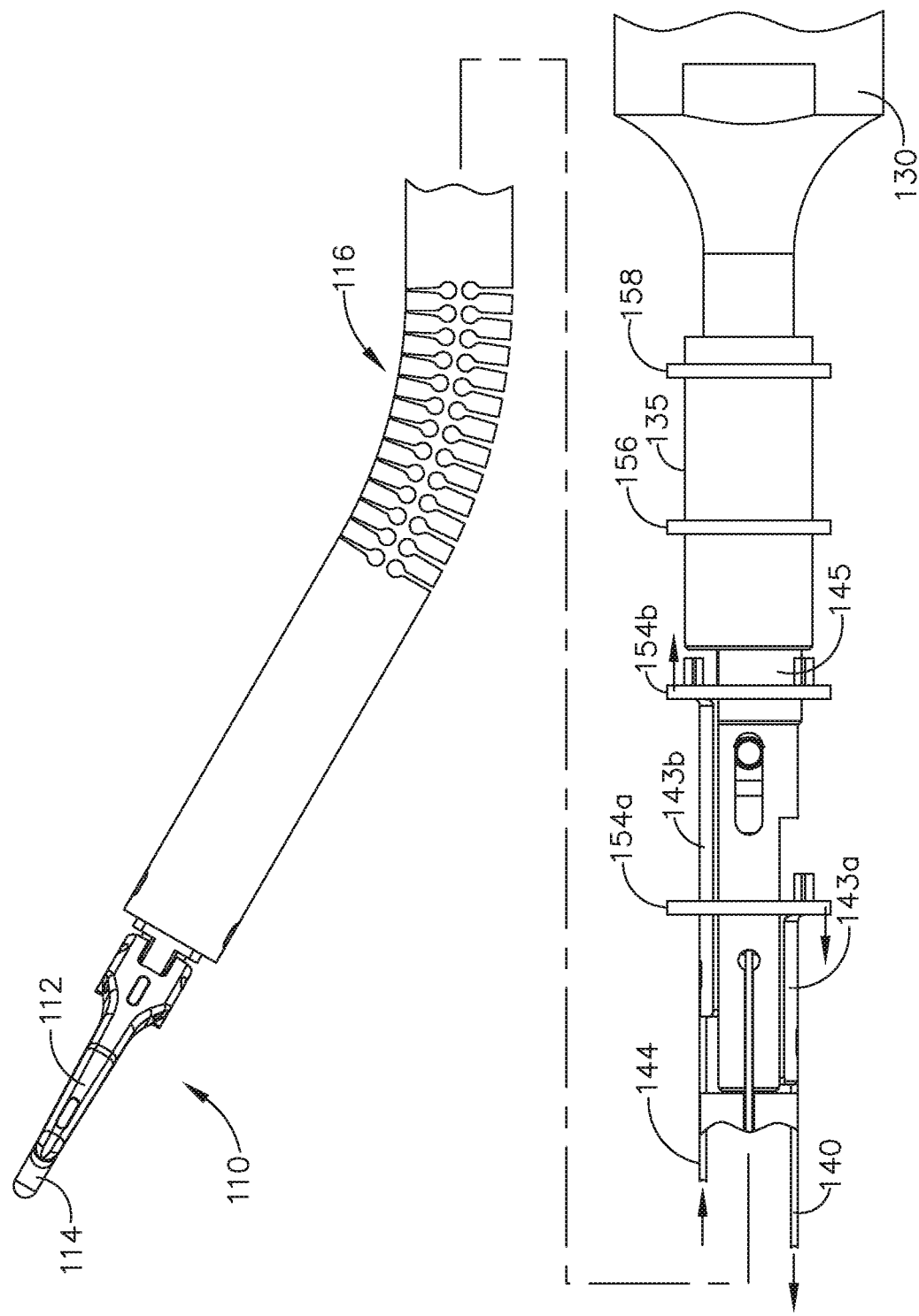
FIG. 14 is a top view of the surgical instrument shown in FIG. 1 with the end effector in a right articulated configuration, according to one aspect of this disclosure.

To articulate the end effector 110 to the right, as shown in FIG. 14, the articulation rotary input 124 is rotated CCW as described in FIG. 2. As the articulation rotary input 124 rotates CCW, the pinion gear 141 simultaneously drives the first articulation rack gear 160a in the distal direction D and drives the second articulation rack gear 162b in the proximal direction P. As described above, the first and second rings 154a, 154b move in the same direction as the first and second racks 132a, 132b, respectively. Accordingly, the left articulation tube section 143a pushes the left articulation rod 140 in the distal D direction P and the right articulation tube section 143b pulls the right articulation rod 144 in the proximal direction P to articulate the end effector 110 to the right as shown in FIG. 14.

Distal Clamp Arm Rotation

Figure 9:
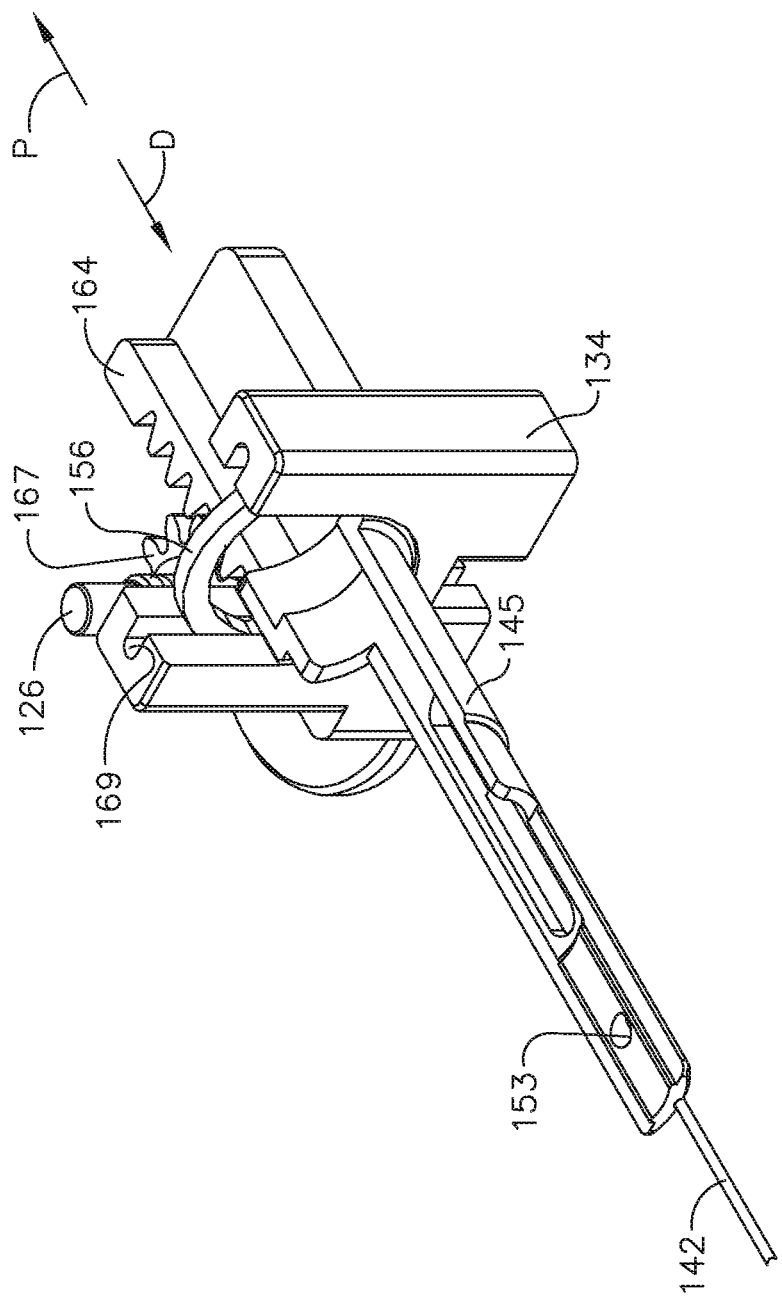
FIG. 9 is a clamp arm rotary input interface and drive section, according to one aspect of this disclosure.

In one aspect, the present disclosure provides mechanisms for rotating the distal clamp arm 112 clockwise or counterclockwise independently of the outer shaft 108. With reference now generally to FIGS. 2-6, 9, 15, 16, and 18, and in particular to FIG. 9, that shows a clamp arm rotary input interface and drive section, according to one aspect of this disclosure. As shown in FIG. 9, the clamp arm roll rotary input 126 includes a pinion gear 167 that engages a clamp arm roll rack gear 164. The clamp arm roll rack gear 164 includes a rack 134 that defines a semiannular groove 169 to receive a ring 156. The ring 156 is attached to a clamp arm roll tube section 145 which is attached to the clamp arm roll rod 142 at a connection 153. The connection 153 may be implemented in any suitable fashion, such as, for example, clevis and pin, solder, weld, threads (male or female), press fit, crimp, swage, rivet, epoxy, or any combinations thereof.

Distal Clamp Arm Rotation Using Spiral Slotted Clamp Arm Roll Tube

FIG. 18 is an exploded view of a distal portion of the robotic ultrasonic surgical instrument 100 comprising a spiral slotted mechanism, according to one aspect of this disclosure. In one aspect, the clamp arm roll rod 142 connects to a pin that is coupled to a rotating clamp arm through a spiral slot. Moving the pin back and forth in the spiral slot rotates the clamp arm and clamp arm pull relative to the shaft. The pin in the spiral slot mechanism gives smooth motion to the clamp arm with infinite stop points. Pulling on the rod connected to the pin rotates the clamp arm one direction and pushing rotates it the opposite direction. The clamp arm closure and distal rotation rods travel along the top and bottom center of the shaft. This location subjects the rods to minimal length change when articulated so that the end effector does not rotate and the clamp arm does not close when the device articulates.

In one aspect, as shown in FIG. 18, the end effector 110 includes a spiral slotted clamp arm roll tube 182 and the clamp arm roll rod 142 is attached to a clamp arm roll pin 186. The distal clamp arm 112 can be rotated clockwise or counterclockwise independently of rotating or articulating the outer shaft 108 or opening or closing the clamp arm 112.

Figure 15:
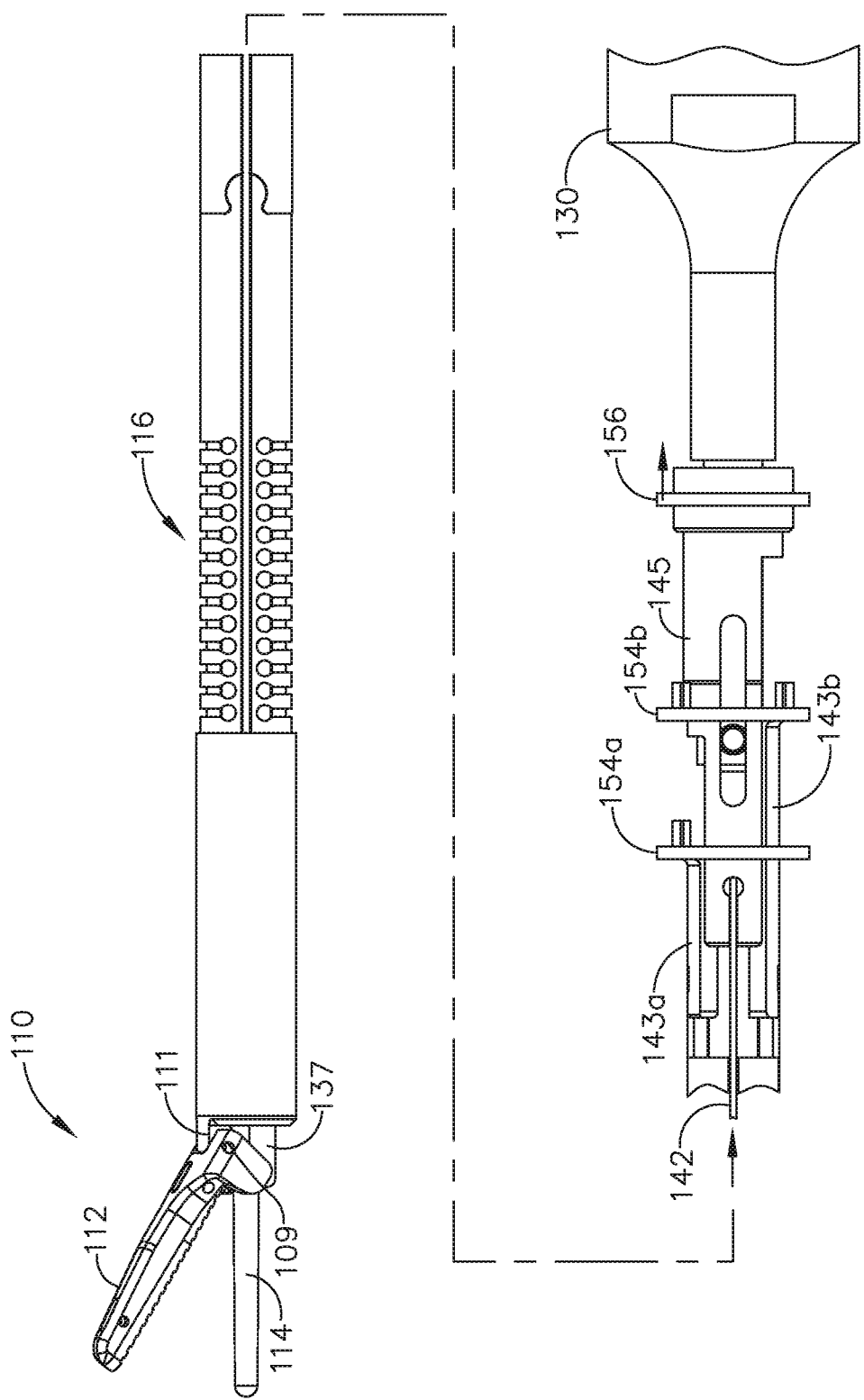
FIG. 15 is a top view of the surgical instrument shown in FIG. 1 with the clamp arm is clockwise rotated configuration, according to one aspect of this disclosure.

To rotate the clamp arm 112 clockwise, the clamp arm roll rotary input 126 is rotated CW as described in FIG. 2. The pinion gear 167 engages the clamp arm roll rack gear 164 to pull the clamp arm roll tube section 145 and the clamp arm roll rod 142 in the proximal direction P as shown in FIG. 15. Clockwise distal rotation of the clamp arm 112 may be implemented by the spiral slotted clamp arm roll tube 182.

Figure 16:
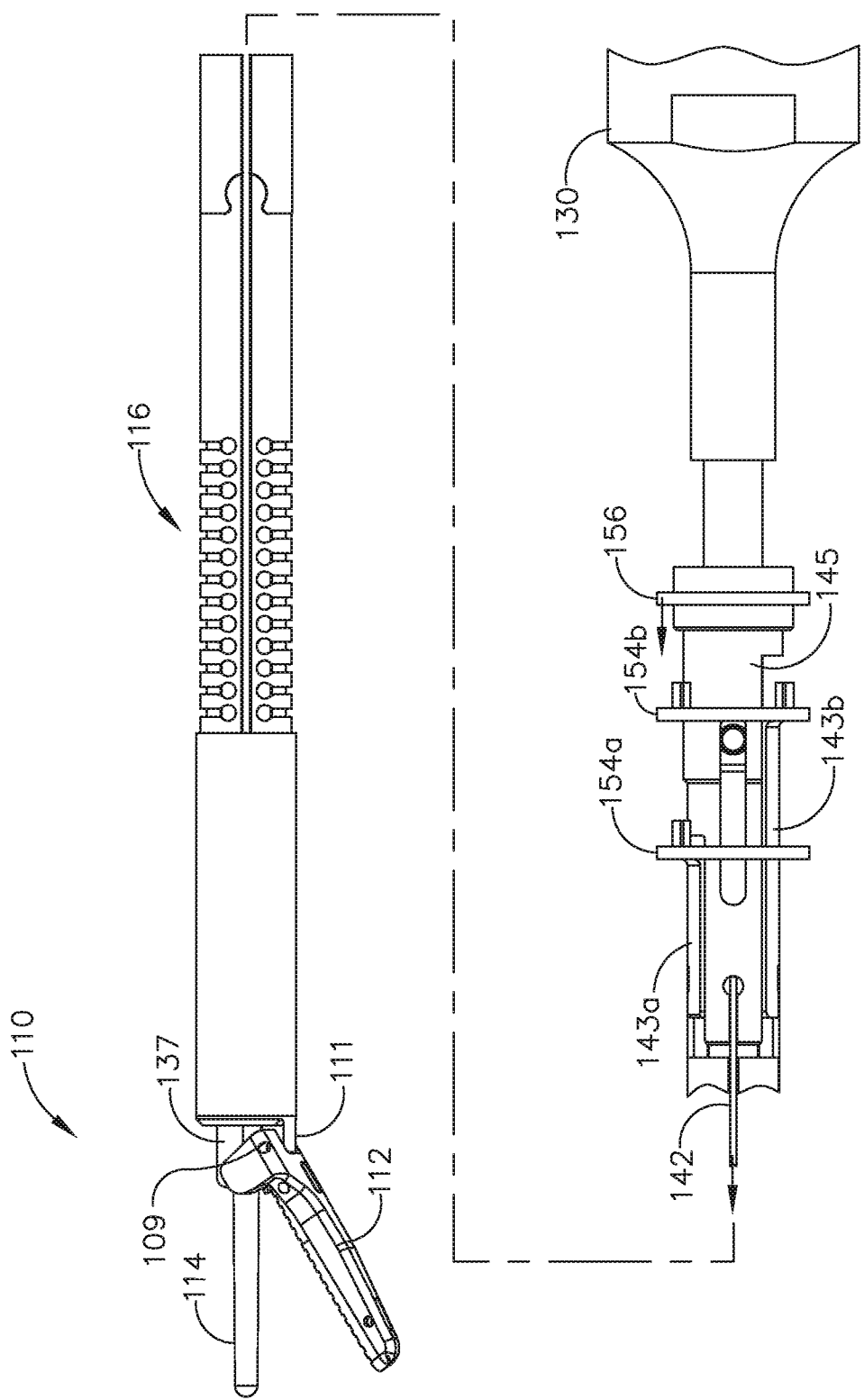
FIG. 16 is a top view of the surgical instrument shown in FIG. 1 with the clamp arm is counterclockwise rotated configuration, according to one aspect of this disclosure.
Figure 17:
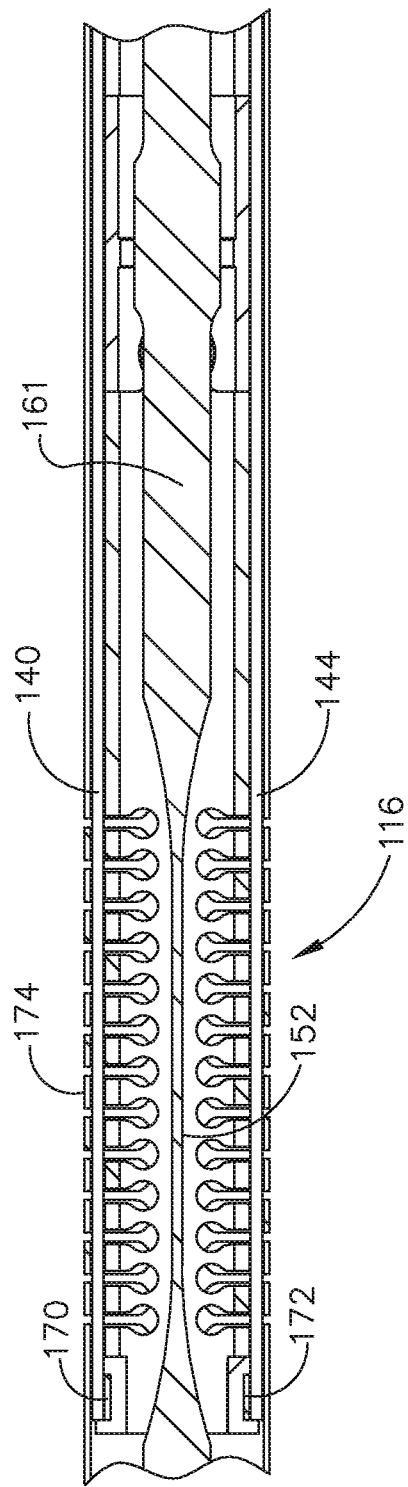
FIG. 17 is a section view of the articulation section of the instrument shown in FIG. 1, according to one aspect of this disclosure.

To rotate the clamp arm 112 counterclockwise, the clamp arm roll rotary input 126 is rotated CCW as described in FIG. 2. The pinion gear 167 engages the clamp arm roll rack gear 164 to push the clamp arm roll tube section 145 and the clamp arm roll rod 142 in the distal direction D as shown in FIG. 16. Counterclockwise distal rotation of the clamp arm 112 also may be implemented by the spiral slotted clamp arm roll tube 182. The spiral slotted clamp arm roll tube 182 aspects of the robotic ultrasonic surgical instrument 100 will be described hereinbelow.

The spiral slotted clamp arm roll tube 182 includes a clamp arm 112 with pins 157a, 157b that engage slots 155a, 155b defined by the closure link 137. The spiral slotted clamp arm roll tube 182 includes a mounting tab 111 defining a hole to receive a pin 109 to rotatably mount the clamp arm 112 to the spiral slotted clamp arm roll tube 182. The spiral slotted clamp arm roll tube 182 is inserted over the rotatable clamp arm closure tube 180 and can freely rotate about the rotatable clamp arm closure tube 180.

The rotatable clamp arm closure tube 180 includes a flange 185 that is rotatably received in a semiannular groove 191 defined at the proximal end of the clamp arm closure coupler 178 as shown in FIGS. 20-23. The clamp arm closure coupler 178 can thus actuate the rotatable clamp arm closure tube 180 to close and open the clamp arm 112 while the rotatable clamp arm closure tube 180 can readily rotate within the semiannular groove 191. The clamp arm closure coupler 178 is positioned over the spiral slotted clamp arm roll tube 182. The clamp arm closure coupler 178 is attached to the clamp arm closure rod 138 at a connection 179.

A spiral slot pin roll rod coupler 187 includes a clamp arm roll pin 186 attached thereto and a connection 189 to attach the clamp arm roll rod 142 thereto. The clamp arm roll pin 186 is slidably received in a spiral slot 184 defined in the spiral slotted clamp arm roll tube 182. The spiral slot pin roll rod coupler 187 is slidably received in a longitudinal slot 107 defined at the bottom of a clamp arm cap 188. The spiral slotted clamp arm roll tube 182 is positioned in the clamp arm cap 188 which is attached to left and right articulation rods 140, 144 that are attached to connections 170, 172, respectively. The clamp arm cap 188 also includes semiannular surface 193 and a semiannular edge 195 to receive corresponding flanges 101, 103 located at the distal end of the spiral slotted clamp arm roll tube 182. A bearing surface 105 defined between the flanges 101, 103 rotatably contacts a bearing 197 defined at a distal end of the clamp arm cap 188 between the semiannular surface 193 and the semiannular edge 195. Tabs 183a, 183b at a distal end of the clamp arm cap 188 are received in corresponding notches 181a, 181b defined at a distal end of the outer shaft 108. The ultrasonic blade 114 is inserted through rotatable clamp arm closure tube 180 and the outer shaft 108 is positioned over the clamp arm cap 188 and the clamp arm closure coupler 178.

Figure 19:
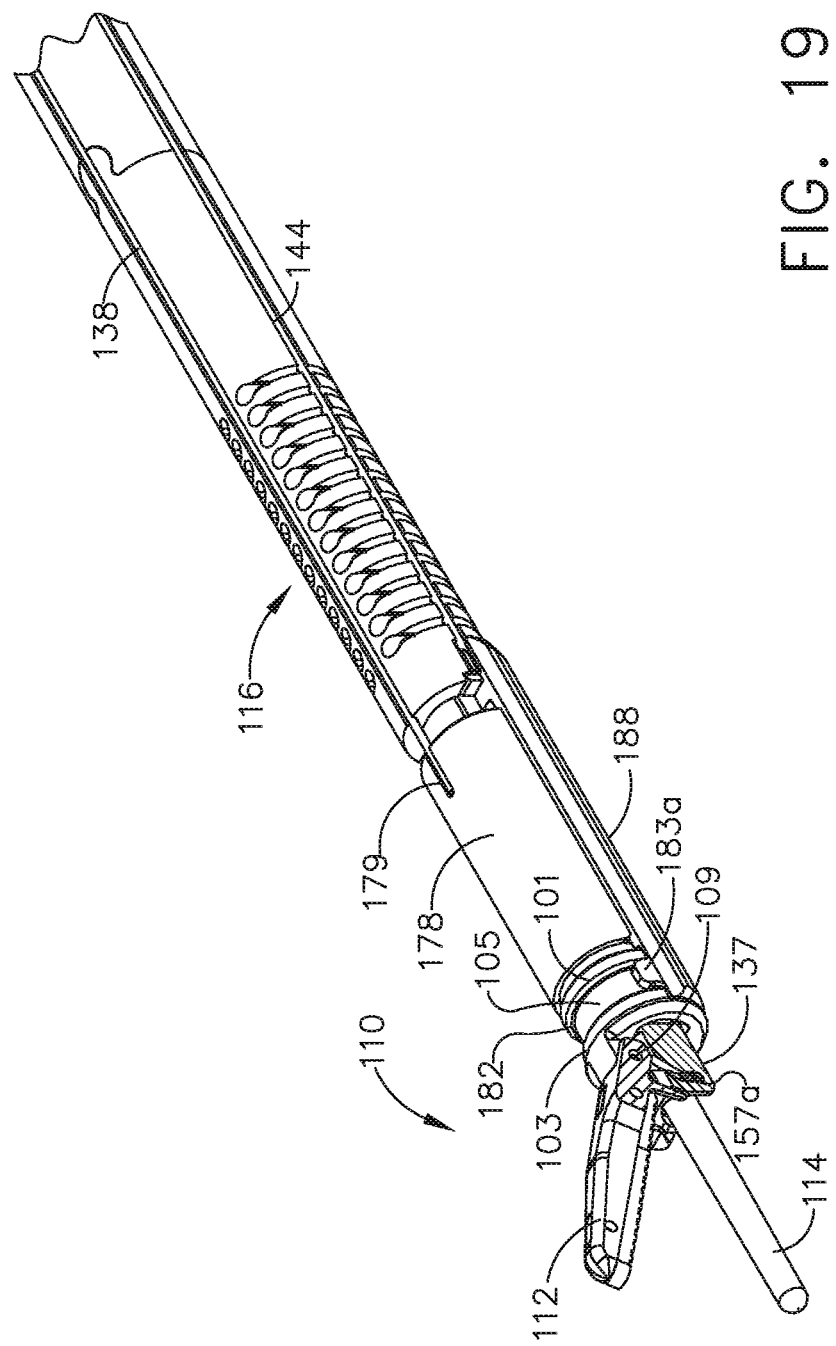
FIG. 19 is a top perspective view of a distal end of the robotic surgical instrument with the outer shaft omitted to expose the top components, according to one aspect of this disclosure.

FIG. 19-23 illustrate an end effector 110 that includes a spiral slotted clamp arm roll tube 182 configured to operate with the robotic ultrasonic surgical instrument 100 according to one aspect of this disclosure. FIG. 19 is a top perspective view of a distal end of the robotic surgical instrument 100 with the outer shaft 108 omitted to expose the top components, according to one aspect of this disclosure. As shown, the clamp arm 112 is in an open position and in a rotational home reference position. The articulation section 116 is in an unarticulated configuration.

Figure 20:
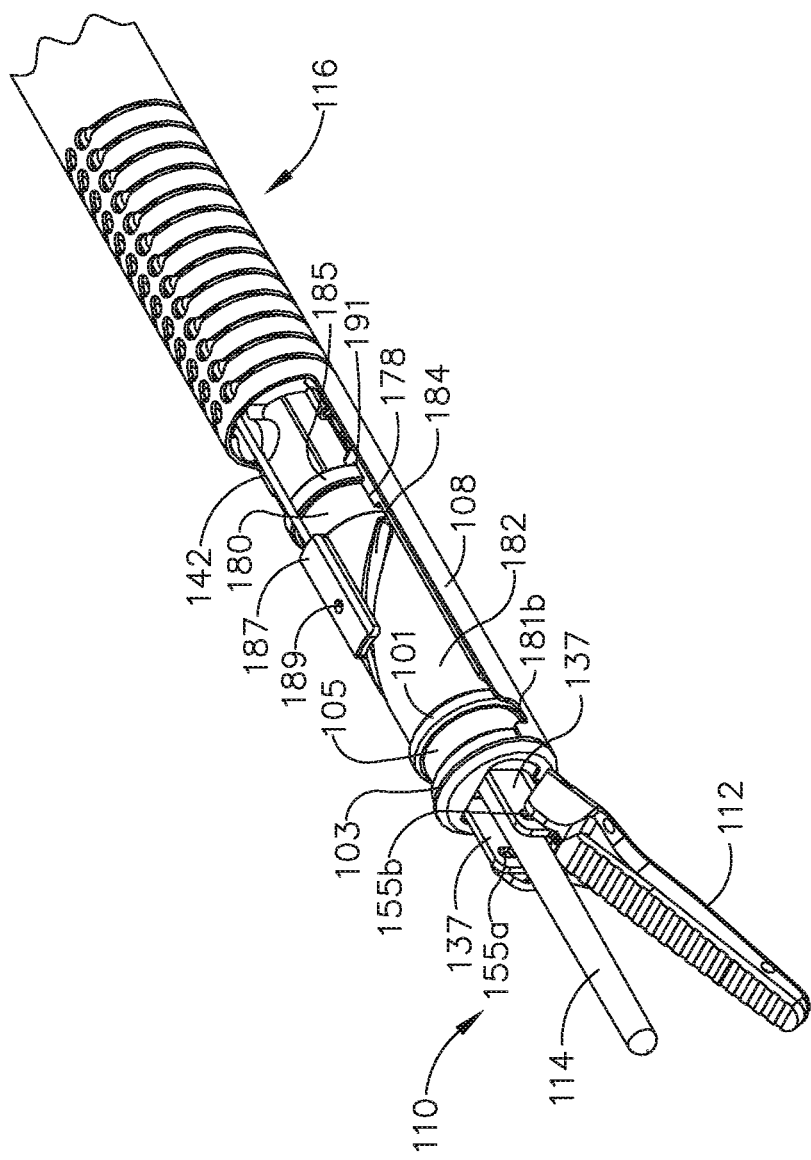
FIG. 20 is a bottom perspective view of a distal end of the robotic surgical instrument with the outer shaft replaced and the clamp arm cap omitted to expose the bottom components, where the end effector is shown in an articulated configuration, according to one aspect of this disclosure.
Figure 23:
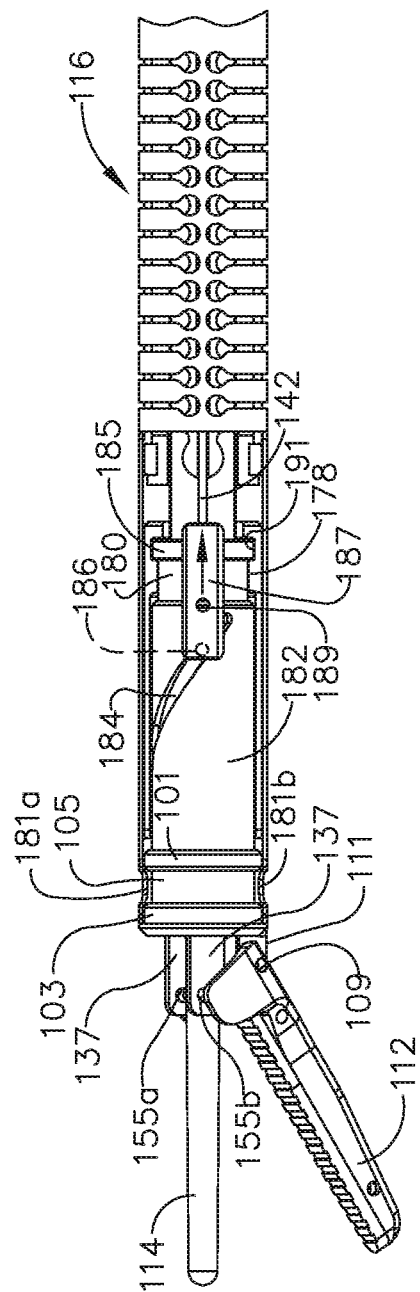
FIG. 23 is a bottom view of a distal end of the robotic surgical instrument shown in FIG. 1 with the outer shaft replaced and the clamp arm cap omitted to expose the bottom components, according to one aspect of this disclosure.

FIG. 20 is a bottom perspective view of a distal end of the robotic surgical instrument 100 with the outer shaft 108 replaced and the clamp arm cap 188 omitted to expose the bottom components, according to one aspect of this disclosure. FIG. 20 illustrates a view of the spiral slotted clamp arm roll tube 182 configuration. The clamp arm 112 is in an open position and in a rotational home reference position as shown in FIG. 19. The articulation section 116 is in an unarticulated configuration. FIG. 23 is a bottom view of a distal end of the robotic surgical instrument 100 with the outer shaft 108 replaced and the clamp arm cap 188 omitted to expose the bottom components, according to one aspect of this disclosure. The articulation section 116 is in an unarticulated configuration.

With now reference to FIGS. 19-23, the spiral slotted clamp arm roll tube 182 is located between a distal portion of the outer shaft 108 and the clamp arm cap 188. The slotted clamp arm roll tube 182 is rotatably positioned over the rotatable clamp arm closure tube 180. The clamp arm closure coupler 178 is slidably attached to the rotatable clamp arm closure tube 180. The flange 185 of the rotatable clamp arm closure tube 180 is rotatably positioned within the semiannular groove 191 defined by the clamp arm closure coupler 178. The rotatable clamp arm closure tube 180 and the spiral slotted clamp arm roll tube 182 are free to rotate. The clamp arm closure coupler 178, the spiral slot pin roll rod coupler 187, and the clamp arm roll pin 186, however, are constrained to move axially along the longitudinal axis. The flanges 101, 103 and the bearing surface 105 on the distal end of the spiral slotted clamp arm roll tube 182 support the spiral slotted clamp arm roll tube 182. A mounting tab 111 is provided on the distal end of the distal flange 103 to attach the clamp arm 112 with a pin 109. The clamp arm 112 is pivotally rotatable about the pin 109 between open and closed positions.

Figure 21:
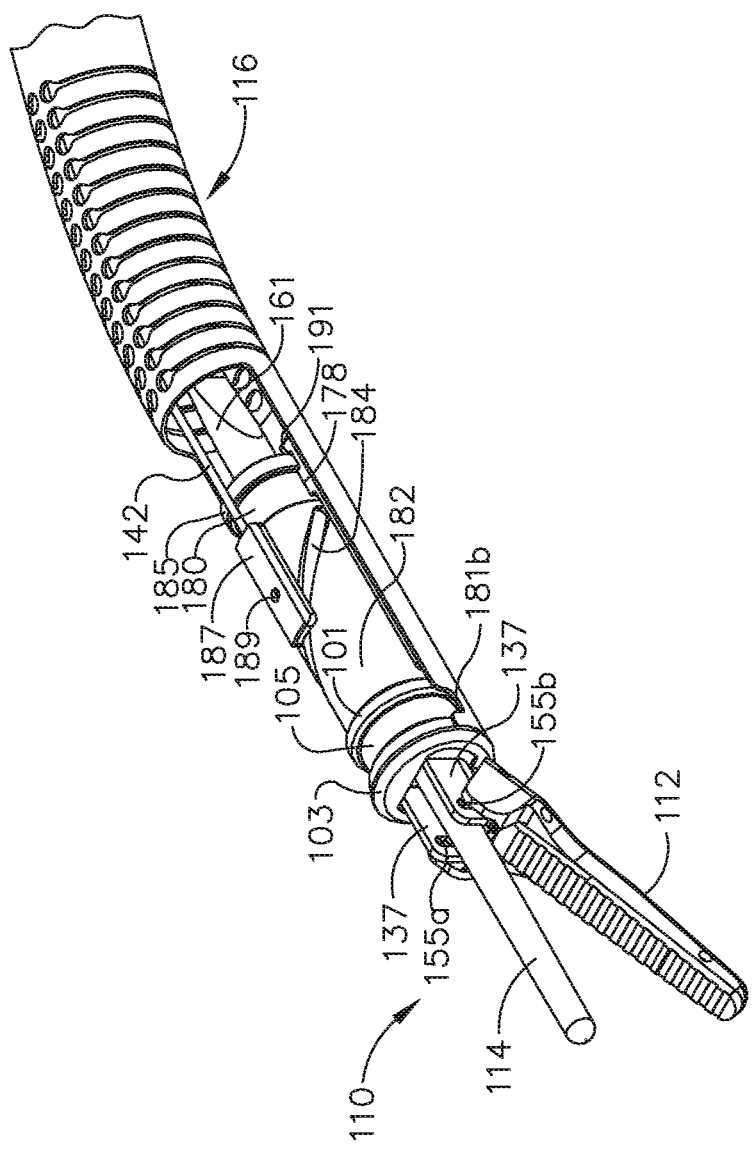
FIG. 21 is a bottom perspective view of a distal end of the robotic surgical instrument with the outer shaft replaced and the clamp arm cap omitted to expose the bottom components, where the end effector is shown in an articulated configuration, according to one aspect of this disclosure.
Figure 22:
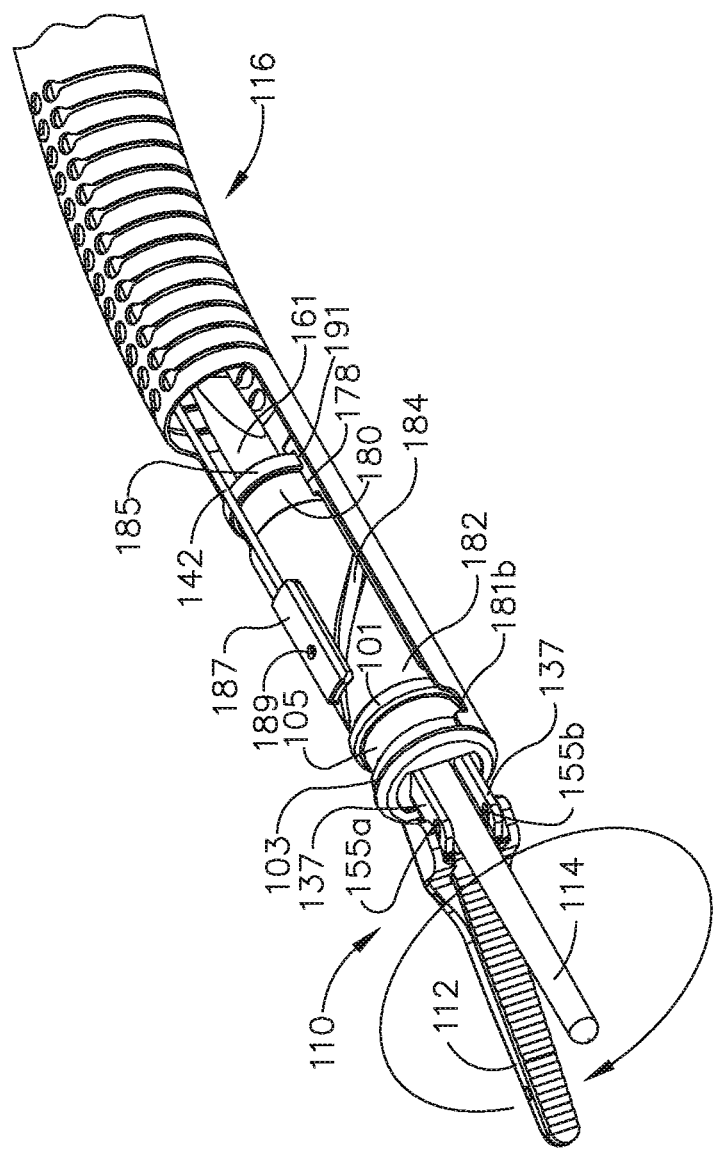
FIG. 22 is a bottom perspective view of a distal end of the robotic surgical instrument with the outer shaft replaced and the clamp arm cap omitted to expose the bottom components, where the end effector is shown in an articulated configuration and the clamp arm is shown in a counterclockwise rotated configuration relative to FIG. 20 according to one aspect of this disclosure.

The rotation of the clamp arm 112 in an articulated configuration relative to the position of the spiral slot pin roll rod coupler 187 and clamp arm roll pin 186 within the spiral slot 184 is described in FIGS. 21 and 22. FIGS. 21 and 22 are bottom perspective view of a distal end of the robotic surgical instrument 100 with the outer shaft 108 replaced and the clamp arm cap 188 omitted to expose the bottom components, according to one aspect of this disclosure. The articulation section 116 is in an articulated configuration and thus the end effector 110 also is in the articulated configuration. As shown in FIG. 21, the spiral slot pin roll rod coupler 187 and clamp arm roll pin 186 are located in a first position along the spiral slot 184 and the clamp arm 112 is rotated in a first rotational position. As shown in FIG. 22, the clamp arm 112 is rotated relative to the position of the clamp arm 112 shown in FIG. 20, where the end effector 110 is shown in an articulated configuration. As shown in FIG. 22, the spiral slot pin roll rod coupler 187 and clamp arm roll pin 186 have been pushed distally to a second position along the spiral slot 184 and the clamp arm 112 is shown rotated counterclockwise in a second rotational position while the end effector 110 remains in the articulated configuration. To rotate the clamp arm 112 clockwise, the spiral slot pin roll rod coupler 187 and clamp arm roll pin 186 pulled back proximally to a more proximal position along the spiral slot 184 and the clamp arm 112. Accordingly, the clamp arm 112 is freely rotatable about the ultrasonic blade 114 independently of the outer shaft 108.

Accordingly, as the clamp arm roll rotary input 126 is rotated CW as described in FIG. 2, the clamp arm roll rod 142 is pulled proximally. As the spiral slot pin roll rod coupler 187 is pulled proximally by the clamp arm roll rod 142, the clamp arm roll pin 186 slidably engages the spiral slot 184 to turn the spiral slotted clamp arm roll tube 182 in a clockwise direction. Conversely, as the clamp arm roll rotary input 126 is rotated CCW as described in FIG. 2, the clamp arm roll rod 142 is pushed distally. As the spiral slot pin roll rod coupler 187 is pushed distally by the clamp arm roll rod 142, the clamp arm roll pin 186 slidably engages the spiral slot 184 to turn the spiral slotted clamp arm roll tube 182 in a counterclockwise direction. During the rotation of the spiral slotted clamp arm roll tube 182, the clamp arm 112 can be closed or opened by the clamp arm closure coupler 178 in cooperation with the rotatable clamp arm closure tube 180. It should be noted that the ultrasonic blade 114 and waveguide 161 do not rotate. Further, the position of the articulation section 116 should be maintained relative to the thin walled section 152 section of the ultrasonic waveguide 161 to enable the end effector 110 to articulate. Advantages of the spiral slotted clamp arm 182 configuration to rotate the distal clamp arm 112 includes its simple design and provides continuous motion with few parts and has infinite stop points in its range.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various aspects have been described herein, many modifications and variations to those aspects may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered examples:

1. A surgical instrument, comprising: a rotatable shaft comprising an articulation section; an ultrasonic waveguide disposed within the shaft, wherein the ultrasonic waveguide is configured to articulate at the articulation section; and a rotatable clamp arm located distal of the articulation section of the rotatable shaft, wherein the rotatable clamp arm is configured to rotate independently of the rotatable shaft distal of the articulation section.

2. The surgical instrument of Example 1, wherein the ultrasonic waveguide comprises an ultrasonic blade tip that is uniformly round.

3. The surgical instrument of one or more of Example 1 through Example 2, wherein the ultrasonic waveguide comprises an ultrasonic blade tip that is partially round and defines a cutting tip on a bottom portion.

4. The surgical instrument of one or more of Example 1 through Example 3, further comprising a spiral slotted clamp arm roll tube coupled to the rotatable clamp arm, wherein the a spiral slotted clamp arm roll tube defines a spiral slot configured to slidably receive a pin, wherein proximal and distal translation of the pin causes the spiral slotted clamp arm roll tube and the clamp arm to rotate about an ultrasonic blade portion of the ultrasonic waveguide independently of the rotatable shaft.

5. The surgical instrument of claim Example 4, further comprising: a clamp arm roll rod; a spiral slot pin roll rod coupler attached to the clamp arm roll rod at a connection; and a pin attached to the spiral slot pin roll rod coupler.

6. The surgical instrument of one or more of Example 4 through Example 6, further comprising a rotatable closure tube located within the spiral slotted clamp arm roll tube, the rotatable closure tube comprising a closure link at a distal end of the rotatable closure tube, wherein the closure link defines slots to receive pins defined by the clamp arm.

7. The surgical instrument of Example 6, further comprising: a clamp arm closure rod; and a coupler attached to the clamp arm closure rod at a connection; wherein the rotatable closure tube defines a flange at a proximal end; and wherein the coupler defines a semiannular groove configured to rotatably receive the flange.

8. The surgical instrument of one or more of Example 4 through Example 7, further comprising: first and second articulation rods; and a clamp arm cap configured to rotatably receive the spiral slotted clamp arm roll tube, wherein the first and second articulation rods are attached to a proximal end of the clamp arm cap at first and second connections.

What is claimed is:

1. A surgical instrument, comprising:
   a rotatable shaft comprising an articulation section;
   an ultrasonic waveguide disposed within the shaft, wherein the ultrasonic waveguide is configured to articulate at the articulation section;
   a rotatable clamp arm located distal of the articulation section of the rotatable shaft, wherein the rotatable clamp arm is configured to rotate independently of the rotatable shaft distal of the articulation section; and
   a spiral slotted clamp arm roll tube coupled to the rotatable clamp arm, wherein the spiral slotted clamp arm roll tube defines a spiral slot configured to slidably receive a pin, wherein proximal and distal translation of the pin causes the spiral slotted clamp arm roll tube and the clamp arm to rotate about an ultrasonic blade portion of the ultrasonic waveguide independently of the rotatable shaft.

2. The surgical instrument of claim 1, wherein the ultrasonic waveguide comprises an ultrasonic blade tip that is uniformly round.

3. The surgical instrument of claim 1, wherein the ultrasonic waveguide comprises an ultrasonic blade tip that is partially round and defines a cutting tip on a bottom portion.

4. The surgical instrument of claim 1, further comprising:
   a clamp arm roll rod;
   a spiral slot pin roll rod coupler attached to the clamp arm roll rod at a connection; and
   a pin attached to the spiral slot pin roll rod coupler.

5. The surgical instrument of claim 1, further comprising a rotatable closure tube located within the spiral slotted clamp arm roll tube, the rotatable closure tube comprising a closure link at a distal end of the rotatable closure tube, wherein the closure link defines slots to receive pins defined by the clamp arm.

6. The surgical instrument of claim 5, further comprising:
a clamp arm closure rod; and
a coupler attached to the clamp arm closure rod at a connection;
wherein the rotatable closure tube defines a flange at a proximal end; and
wherein the coupler defines a semiannular groove configured to rotatably receive the flange.

7. The surgical instrument of claim 1, further comprising:
first and second articulation rods; and
a clamp arm cap configured to rotatably receive the spiral slotted clamp arm roll tube, wherein the first and second articulation rods are attached to a proximal end of the clamp arm cap at first and second connections.

8. The surgical instrument of claim 1, wherein the clamp arm is configured to pivot towards and away from the ultrasonic blade portion when the articulation section is in an articulated configuration.

9. The surgical instrument of claim 1, wherein the clamp arm is configured to rotate about the ultrasonic blade portion when the articulation section is in an articulated configuration.

* * * * *